United States Patent [19]

Marquis et al.

[11] Patent Number: 4,891,437

[45] Date of Patent: Jan. 2, 1990

[54] OLEFIN EPOXIDATION OF OLEFINS IN A POLAR MEDIUM

[75] Inventors: Edward T. Marquis; Kenneth P. Keating; John F. Knifton; William A. Smith, all of Austin; John R. Sanderson, Leander; Jonathan P. Lustri, Austin, all of Tex.

[73] Assignee: Texaco Inc., White Plains, N.Y.

[21] Appl. No.: 133,664

[22] Filed: Dec. 16, 1987

Related U.S. Application Data

[63] Continuation of Ser. No. 797,079, Nov. 15, 1985, abandoned, which is a continuation-in-part of Ser. No. 687,709, Dec. 31, 1984, abandoned, Ser. No. 687,678, Dec. 31, 1984, abandoned, Ser. No. 687,790, Dec. 31, 1984, abandoned, and Ser. No. 687,702, Dec. 31, 1984, abandoned.

[51] Int. Cl.$^4$ ............................................. C07D 301/19
[52] U.S. Cl. ..................................................... 549/529
[58] Field of Search .......................................... 549/529

[56] References Cited

U.S. PATENT DOCUMENTS

| Re. 31,381 | 9/1983 | Prescher et al. | |
|---|---|---|---|
| 3,418,340 | 12/1968 | Russell | 260/348.5 |
| 3,480,563 | 11/1969 | Bonetti et al. | 252/431 |
| 3,801,667 | 11/1971 | Schneider | 260/680 |
| 3,836,603 | 9/1974 | Conner et al. | 260/673.5 |
| 4,113,747 | 9/1978 | Prescher et al. | |
| 4,137,242 | 1/1979 | Prescher et al. | |
| 4,217,287 | 8/1980 | Wu et al. | 260/348 |

OTHER PUBLICATIONS

Wu et al., J. of Catalysis, vol. 43 (1976), pp. 380–383.
Sheldon, Recueil, vol. 92 (1973), pp. 253–266.
Sheldon, Recueil, vol. 92 (1973), pp. 367–373.
Sheldon, J. Catalysis, vol. 31 (1973), pp. 438–443.
Sheldon, J. Catalysis, vol. 31 (1973), pp. 427–437.
Sheldon, J. Mol. Catalysis, vol. 7 (1980), ppl. 107–126.
Ward, J. Mol. Catalysis, vol. 27 (1984), p. 7.
Sheldon, J. Mol. Catalysis, vol. 20 (1983), pp. 1–26.
Rico, A.C.S. Div. of Pet. Chem., 1980, 25 (3), pp. 433–437.
Sheng, Advances Chemists Science, 76 (1968), pp. 418–430.
Gould, JACS, 90 (1968), pp. 4573–4579.

Primary Examiner—Glennon H. Hollrah
Assistant Examiner—Amelia A. Owens
Attorney, Agent, or Firm—Jack H. Park; Kenneth R. Priem; Carl G. Ries

[57] ABSTRACT

A hydroperoxide charge stock (t-butyl hydroperoxide or t-amyl hydroperoxide) is reacted with a $C_3$ to $C_{20}$ olefin charge stock in liquid phase in a reaction zone in the presence of a catalytically effective amount of a soluble molybdenum catalyst to form a product olefin epoxide corresponding to the olefin charge stock and a product alcohol corresponding to the hydroperoxide charge (t-butyl alcohol or t-amyl alcohol), which process is improved in accordance with the present invention by maintaining a reaction medium composed of more than 60 wt % of polar components (hydroperoxide charge stock, product alcohol and product epoxide) in the reaction zone by charging to the reaction zone at least about a 30 wt % solution of the hydroperoxide charge stock in the corresponding product alcohol and charging said olefin charge stock to said reaction zone in an amount relative to the amount of said charged solution of charged hydroperoxide in product alcohol sufficient to provide a ratio of from about 0.5 to about 2 moles of charged olefin per mole of charged hydroperoxide.

The preferred olefin charge stock is propylene and the preferred hydroperoxide charge stock is t-butyl hydroperoxide. The corresponding epoxide in this situation is propylene oxide and the corresponding product alcohol is t-butyl alcohol.

25 Claims, No Drawings

OLEFIN EPOXIDATION OF OLEFINS IN A POLAR MEDIUM

CROSS-REFERENCE TO RELATED APPLICATIONS

This application is a continuation of Marquis et al. U.S. patent application Ser. No. 06/797,079 filed Nov. 15, 1985, and entitled "Olefin Epoxidation in a Polar Medium" now abandoned is a continuation-in-part of copending application Ser. No. 06/687,709 filed Dec. 31, 1984, and entitled "Improved Epoxidation Process Using Molybdenum Catalysts", now abandoned of copending application Ser. No. 06/687,678 filed Dec. 31, 1984, and entitled "Improved Epoxidation Process Providing Low Olefin Oligomer By-Product Formation", now abandoned copending application Ser. No. 06/687,690 filed Dec. 31, 1984, and entitled "Improved Epoxidation Using Low Olefin to Hydroperoxide Ratios" now abandoned and of copending U.S. patent application Ser. No. 06/687,702, filed Dec. 31, 1984, and entitled "Reactor Configuration for Propylene Oxide Production Process" now abandoned.

BACKGROUND OF THE INVENTION

1. Field of the Invention

This invention relates to the molybdenum-catalyzed epoxidation of $C_3$ to $C_{20}$ olefins with tertiary butyl hydroperoxide or tertiary amyl hydroperoxide in liquid phase in a polar reaction medium.

2. Prior Art

The epoxidation of olefins to give various oxide compounds has long been an area of study by those skilled in the art. It is well known that the reactivities of the various olefins differs with the number of substituents on the carbon atoms involved in the double bond. Ethylene itself has the lowest relative rate of epoxidation, with propylene and other alpha olefins being the next slowest. Compounds of the formula $R_2C=CR_2$ where R simply represents alkyl or other substituents may be epoxidized fastest.

Of course, the production of ethylene oxide from ethylene has long been known to be accomplished by reaction with molecular oxygen over a silver catalyst. Numerous patents have issued on various silver-catalyzed processes for the production of ethylene oxide.

Unfortunately, the silver catalyst route is poor for olefins other than ethylene. For a long time the commercial production of propylene oxide could only be accomplished via the cumbersome chlorohydrin process.

Another commercial process for the manufacture of substituted oxides from alpha olefins such as propylene was not discovered until U.S. Pat. No. 3,351,635 taught that an organic oxide compound could be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. U.S. Pat. No. 3,350,422 teaches a similar process using a soluble vanadium catalyst. Molybdenum is the preferred catalyst. A substantial excess of olefin relative to the hydroperoxide is taught as the normal procedure for the reaction. See also U.S. Pat. No. 3,526,645 which teaches the slow addition of organic hydroperoxide to an excess of olefin as preferred.

However, even though this work was recognized as extremely important in the development of a commercial propylene oxide process that did not depend on the chlorohydrin route, it has been recognized that the molybdenum process has a number of problems. For example, large quantities of the alcohol corresponding to the peroxide used were formed; if t-butyl hydroperoxide was used as a co-reactant, then a use or market for t-butyl alcohol is required. With propylene, various undesirable propylene dimers, sometimes called hexenes, are formed. Besides being undesirable in that propylene is consumed, problems are caused in separating the desired propylene oxide from the product mix. In addition, the molybdenum catalyst may not be stable or the recovery of the catalyst for recycle may be poor.

A number of other methods for the production of alkylene oxides from epoxidizing olefins (particularly propylene) have been proposed. U.S. Pat. No. 3,666,777 to Sargenti reveals a process for epoxidizing propylene using a molybdenum-containing epoxidation catalyst solution prepared by heating molybdenum powder with a stream containing unreacted tertiary butyl hydroperoxide used in the epoxidation process as the oxidizing agent and polyhydric compounds. The polyhydric compounds are to have a molecular weight from 200 to 300 and are to be formed as a by-product in the epoxidation process. A process for preparing propylene oxide by direct oxidation of propylene with an organic hydroperoxide in the presence of a catalyst (such as molybdenum or vanadium) is described in British Patent No. 1,338,015 to Atlantic-Richfield. The improvement therein resides in the inclusion of a free radical inhibitor in the reaction mixture to help eliminate the formation of $C_5$ to $C_7$ hydrocarbon by-products which must be removed by extractive distillation. Proposed free radical inhibitors are tertiary butyl catechol and 2,6-di-t-butyl-4-methyl phenol.

Stein, et al. in U.S. Pat. No. 3,849,451 have improved upon the Kollar process of U.S. Pat. Nos. 3,350,422 and 3,351,635 by requiring a close control of the reaction temperature, between 90–200° C. and autogeneous pressures, among other parameters. Stein et al. also suggest the use of several reaction vessels with somewhat higher temperatures in the last zones to insure more complete reaction. The primary benefits seem to be improved yields and reduced side reactions. Prescher et al. in U.S. Reissue Pat. No. Re.31,381 disclose a process for the preparation of propylene oxide from propylene and hydrogen peroxide wherein plural reactors such as stirred kettles, tubular reactors and loop reactors may be used. They recommend, as an example, the use of a train of several stirred kettles, such as a cascade of 3 to 6 kettle reactors or the use of 1 to 3 stirred kettles arranged in series followed by a tubular reactor.

Russell U.S. Pat. No. 3,418,430 discloses a process for producing propylene oxide by reacting propylene with an organic hydroperoxide in solvent solution in the presence of a metallic epoxidation catalyst, such as a compound of molybdenum at a mole ratio of propylene to hydroperoxide of 0.5:1 to 100:1 (preferably 2:1 to 10:1) at a temperature of −20° to 200° C. (preferably 50–120° C.) and a pressure of about atmospheric to 1000 psia, with a low olefin conversion per pass (e.g., 10–30%) wherein unreacted oxygen is removed from the unreacted propylene.

Sheng et al. U.S. Pat. No. 3,434,975 discloses a method for making molybdenum compounds useful to catalyze the reaction of olefins with organic hydroperoxides wherein metallic molybdenum is reacted with an organic hydroperoxide, such as tertiary butyl hydroperoxide, a peracid or hydrogen peroxide in the presence of a saturated $C_1$–$C_4$ alcohol.

The molybdenum-catalyzed epoxidation of alpha olefins and alpha substituted olefins with relatively less stable hydroperoxides may be accomplished according to U.S. Pat. No. 3,862,961 to Sheng, et al. by employing a critical amount of a stabilizing agent consisting of a $C_3$ to $C_9$ secondary or tertiary monohydric alcohol. The preferred alcohol seems to be tertiary butyl alcohol. Citric acid is used to minimize the iron-catalyzed decomposition of the organic hydroperoxide without adversely affecting the reaction between the hydroperoxide and the olefin in a similar oxirane producing process taught by Herzog in U.S. Pat. No. 3,928,393. The inventors in U.S. Pat. No. 4,217,287 discovered that if barium oxide is present in the reaction mixture, the catalytic epoxidation of olefins with organic hydroperoxides can be successfully carried out with good selectivity to the epoxide based on hydroperoxide converted when a relatively low olefin to hydroperoxide mole ratio is used. The alpha-olefinically unsaturated compound must be added incrementally to the organic hydroperoxide to provide an excess of hydroperoxide that is effective.

Selective epoxidation of olefins with cumene hydroperoxide (CHP) can be accomplished at high CHP to olefin ratios if barium oxide is present with the molybdenum catalyst as reported by Wu and Swift in "Selective Olefin Epoxidation at High Hydroperoxide to Olefin Ratios," *Journal of Catalysis*, Vol. 43, 380–383 (1976).

Catalysts other than molybdenum have been tried. Copper polyphthalocyanine which has been activated by contact with an aromatic heterocyclic amine is an effective catalyst for the oxidation of certain aliphatic and alicyclic compounds (propylene, for instance) as discovered by Brownstein, et al. described in U.S. Pat. No. 4,028,423.

Various methods for preparing molybdenum catalysts useful in these olefin epoxidation methods are described in the following patents: U.S. Pat. No. 3,362,972 to Kollar; U.S. Pat. No. 3,480,563 to Bonetti, et al.; U.S. Pat. No. 3,578,690 to Becker; U.S. Pat. No. 3,953,362 and U. S. Pat. No. 4,009,122 both to Lines, et al.

It has also been proposed to use the tertiary butyl alcohol that is formed when propylene is reacted with tertiary butyl hydroperoxide as an intermediate in the synthesis of another organic compound. Thus, Schneider, in U.S. Pat. No. 3,801,667, proposes a method for the preparation of isoprene wherein, as the second step of a six step process, tertiarybutyl hydroperoxide is reacted with propylene in accordance with U.S. Pat. No. 3,418,340 to provide tertiary butyl alcohol. Connor et al. in U.S. Pat. No. 3,836,603 propose to use the tertiary butyl alcohol as an intermediate in a multi-step process for the manufacture of p-xylene.

Also pertinent to the subject discovery are those patents which address schemes for separating propylene oxide from the other by-products produced. These patents demonstrate a high concern for separating out the useful propylene oxide from the close boiling hexene oligomers. It would be a great progression in the art if a method could be devised where the oligomer by-products would be produced not at all or in such low proportions that a separate separation step would not be necessary as in these patents.

U.S. Pat. No. 3,464,897 addresses the separation of propylene oxide from other hydrocarbons having boiling points close to propylene oxide by distilling the mixture in the presence of an open chain or cyclic paraffin containing from 8 to 12 carbon atoms. Similarly, propylene oxide can be separated from water using identical entrainers as disclosed in U.S. Pat. No. 3,607,669. Propylene oxide is purified from its by-products by fractionation in the presence of a hydrocarbon having from 8 to 20 carbon atoms according to U.S. Pat. No. 3,843,488. Additionally, U.S. Pat. No. 3,909,366 teaches that propylene oxide may be purified with respect to contaminating paraffinic and olefinic hydocarbons by extractive distillation in the presence of an aromatic hydrocarbon having from 6 to 12 carbon atoms.

SUMMARY OF THE INVENTION

This invention is directed to a process wherein a hydroperoxide charge stock (t-butyl hydroperoxide, TBHP or t-amyl hydroperoxide), TAHP is reacted with a $C_3$ to $C_{20}$ olefin charge stock in liquid phase in a reaction zone in the presence of a catalytically effective amount of a soluble molybdenum catalyst to form a product olefin epoxide corresponding to the olefin charge stock and a product alcohol corresponding to the hydroperoxide charge (t-butyl alcohol or t-amyl alcohol), which process is improved in accordance with the present invention by maintaining a reaction medium composed of more than 60 wt. % of polar components (hydroperoxide charge stock, product alcohol and product epoxide) in the reaction zone by charging to the reaction zone at least about a 30 wt. % solution of the hydroperoxide charge stock in the corresponding product alcohol and charging said olefin charge stock to said reaction zone in an amount relative to the amount of said charged solution of charged hydroperoxide in product alcohol sufficient to provide a ratio of from about 0.5 to about 2 moles of charged olefin per mole of charged hydroperoxide.

The preferred olefin charge stock is propylene and the preferred hydroperoxide charge stock is t-butyl hydroperoxide. The corresponding epoxide in this situation is propylene oxide and the corresponding product alcohol is t-butyl alcohol.

BACKGROUND OF THE INVENTION

Under ambient conditions t-butyl hydroperoxide and t-amyl hydroperoxide are comparatively stable materials. However, as temperature increases, these hydroperoxides tend to become "destabilized" so that thermal and/or catalytic decomposition will be initiated leading to the formation of unwanted by-products such as ketones, lower molecular weight alcohols, tertiary alcohols, oxygen, etc. This is a particularly troublesome problem at temperatures of 50° to 180° C. (e.g., 100° to 130° C.) which are normally used when such a hydroperoxide is catalytically reacted with an olefin to form an olefin epoxide. This problem can be at least partially overcome by conducting the epoxidation reaction in the presence of an excess of the olefin reactant. However, the unreacted olefin must be separated from the epoxide reaction product for recycle and such separations are accomplished with progressively more difficulty as the molecular weight of the olefin reactant increases. Problems can be encountered even with the lower molecular weight olefins and, in any event, the utility costs associated with the recovery and recycle of significant quantities of the olefin reactant add an appreciable burden to the cost of manufacture of the corresponding olefin epoxide and alcohol reaction products.

Further, use of excess propylene in order to increase reaction rate and therefore reduce the side reactions of TBHP or TAHP leads to the serious problem of propylene dimer formation. The formation of dimer is a second order reaction and hence is accelerated as the concentration of propylene increases. Also, the use of excess propylene affords a more non-polar medium which in turn tends to render the molybdenum catalyst less soluble during the reaction.

DETAILED DESCRIPTION OF THE PREFERRED EMBODIMENT

It has been discovered in accordance with the present invention that, in the production of olefin epoxides by reacting a $C_3$–$C_{20}$ olefin with t-butyl hydroperoxide or t-amyl hydroperoxide in liquid phase in the presence of a catalytically effective amount of a soluble molybdenum catalysts, an unexpectedly high selectivity to olefin epoxide, on the basis of hydroperoxide converted, can be obtained when the hydroperoxide is charged to the reaction zone in at least a 30 wt. % solution of the corresponding product alcohol and the olefin is charged to the reaction zone in an amount relative to the hydroperoxide charged to the reaction zone such that about 0.5 to 2 moles of olefin are charged per mole of hydroperoxide charged.

Reactants and Catalysts

The method of this invention can be used to epoxidize $C_3$–$C_{20}$ olefinically unsaturated compound such as substituted and unsubstituted aliphatic and alicyclic olefins. The process is particularly useful in epoxidizing compounds having at least one double bond situated in the alpha position of a chain or internally. Representative compounds include propylene, normal butylene, isobutylene, pentenes, methyl pentenes, hexenes, octenes, dodecenes, cyclohexene, substituted cyclohexenes, butadiene, styrene, substituted styrenes, vinyl toluene, vinyl cyclohexene, phenyl cyclohexenes and the like.

The invention finds its greatest utility in the epoxidation of primary or alpha olefins and propylene is epoxidized particularly advantageously by the inventive process.

It has been surprisingly discovered that the method of this invention does not work equally well for all hydroperoxides. For example, with cumene hydroperoxide at low propylene excesses, the selectivity to propylene oxide, based on cumene hydroperoxide converted is poor.

Tertiary butyl hydroperoxide (TBHP) and tertiary amyl hydroperoxide (TAHP) are the hydroperoxides to be used in accordance with the present invention. Tertiary butyl hydroperoxide is preferred.

The TBHP should be charged in at least a 30 wt. % solution in t-butyl alcohol, and preferably about a 40 to 75 wt. % solution.

Catalysts suitable for the epoxidation method of this invention are molybdenum catalysts that are soluble in the reaction medium.

Examples of suitable soluble catalysts include molybdenum compounds such as molybdenum octoate, molybdenum naphthenate, molybdenum acetyl acetonate, molybdenum/alcohol complexes, molybdenum/glycol complexes, etc.

Other catalysts found to be useful are the molybdenum complexes of alkylene glycols with molybdenum compounds as described in co-pending patent application Ser. No. 06/687,701, filed Dec. 31, 1985, now U.S. Pat. No. 4,626,506 incorporated by reference herein. Briefly, these complexes are made by reacting an ammonium-containing molybdenum compound with an alkylene glycol in the presence of water at an elevated temperature, such as about 80 to 130° C. The ammonium-containing molybdenum compound is preferably ammonium heptamolybdate tetrahydrate or ammonium dimolybdate hydrate. The alkylene glycols are preferably ethylene glycol and/or propylene glycol although others have been found to be useful.

Still other catalysts found to be useful in the practice of the present invention are molybdenum complexes of monohydric alcohols as described in copending patent application Ser. No. 06/687,710, filed Dec. 31, 1984, and entitled "Improved Synthesis of Molybdenum/Alcohol Complexes useful as Epoxidation Catalysts", incorporated by reference herein now abandoned in favor of allowed continuation-in-part application Ser. No. 06/804,131 filed Dec. 6, 1985 (now U.S. Pat. No. 4,650,886) and entitled "Synthesis of Ammonium Molybdate/Alkanol Complexes" and copending allowed application Ser. No. 06/804,132 filed Dec. 6, 1985 and entitled "Synthesis of Molybdenum Oxide/Alkanol Complexes" (now U.S. Pat. No. 4,654,427). Briefly, an alkanol such as 2-ethyl hexanol is reacted with a molybdenum oxide in the presence of ammonium hydroxide or by reacting the alkanol with ammonium heptamolybdate in the presence of a controlled amount of water.

Reaction Conditions

The epoxidation reaction may be conducted at a temperature in the range of 50–180° C. with a preferred range of between 90 and 140° C. An especially preferred range is 100 to 130° C. with about 110° C.–120° C. being the most preferred single stage operating temperature.

It has been discovered that the use of only a small molar excess of olefin contributes to increased oxide concentrations, increased oxide selectivities and yields increased recoverable molybdenum. These benefits are due to the more polar reaction media (low propylene, high TBHP/TBA) which tends to stabilize TBHP and render the molybdenum catalyst more active and soluble throughout the entire reaction period. The lower temperatures of our invention further contribute to the catalyst's stability and prevents TBHP decomposition via undesired pathways.

The catalyst concentrations in the method of this invention should be in the range of 50 to 1,000 ppm (0.01 to 0.10 wt. %) based on the total reactant charge. Catalyst concentration is calculated as molybdenum metal. A preferred range is 200 to 600 ppm. Generally, about 250–500 ppm is the most preferred level. These catalyst levels are higher than those presently used in prior art methods, which tend to run from 50 to 200 ppm. Moreover, it has been discovered that the method of the present invention provides a process wherein the molybdenum catalyst is retained in solution in the medium during the life of the reaction.

The epoxidation reaction of this invention is carried out in the presence of a polar solvent. The polar solvent should correspond to the hydroperoxide reactant (i.e., have the same carbon skeleton as the hydroperoxide).

Tertiary butyl hydroperoxide and TBA are coproduced commercially by the oxidation of isobutane and if TBHP is used as the hydroperoxide, TBA is the polar solvent. The TBA coproduced with the TBHP will normally supply all of the polar solvent required for the present invention.

It is preferred that the solution of TBHP in TBA contain very little water, between zero and 1 wt. %. Preferably, the water level should be less than 0.5 wt. %.

The reaction can be carried out to achieve a hydroperoxide conversion, typically 96 to 99%, while still maintaining high epoxide selectivities, typically also 96 to 99% basis the hydroperoxide reacted. For both of these values to be simultaneously so high is very unusual. This is important because the profitability of a commercial olefin epoxide plant, to a significant extent, is increased as the yield of olefin epoxide increases.

The reaction time may vary considerably, from minutes to hours. Generally, the reaction times run from thirty minutes to three or four hours with 1.5–2.0 hours being about average. The preferred single stage reaction time/temperature is two hours at 110–120° C. Preferably the reaction is conducted in two or more temperature stages.

The reaction procedure generally begins by charging the olefin to the reaction vessel. Next, the hydroperoxide, polar solvent and catalyst may be added and the contents heated to the desired reaction temperature. Alternatively, the olefin reactant may be heated to, at or near the preferred reaction temperature, and then the hydroperoxide, polar solvent and catalyst may be added. Further heat may be provided by the exotherm of the reaction. The reaction is then allowed to proceed for the desired amount of time at the reaction temperature, generally 110–120° C., or conducted for 1 hour at 50–120° C. followed by 1 hour at 120–150° C. The mixture is cooled down and the oxide recovered. Generally, for the method of this invention, the oxide concentration runs from about 24–28% for propylene/TBHP mole ratio of 1.6–1.9:1 (TBHP wt. % is 68–80%) and from about 31–32% for propylene/TBHP mole ratio of 1.1:1–1.2:1 (TBHP content is 68–80 wt. %).

A series of reactors helps to achieve the objectives of high reaction medium polarity and low olefin concentration. The use of staged reactors makes it possible to stage the addition of olefin to thereby increase reactor medium polarity and in the case of propylene, to further decrease the formation of propylene dimer. This concept can be further improved by using a continuously stirred tank ractor (CSTR) or a series of CSTR's because a CSTR inherently provides a lower concentration of reactants than a plug flow reactor (PFR).

A more effective approach is to us a CSTR or a series of CSTR's followed by one or more plug flow reactors because conversion can be more effectively forced to completion in a plugged flow reactor.

It is possible and, indeed, desirable to operate each stage at a progressively higher temperature.

As an example, the CSTR may be operated at a temperature in the range of about 70 to 115° C., 90 to 115° C. being preferred, with 100–110° C. as the most preferred reaction temperature range. The PFR should be operated at a higher temperature, from over 115° C. to 150° C., with 120–140° C. as the most preferred range. The plug from reactor can be of any of a number of designs known to those skilled in the art such as jacketed reactors, with heat transfer, adiabatic reactors and combinations thereof. The effluent from the CSTR may be termed an intermediate reaction mixture since the reaction is not complete. The residence time of the reactants in each reactor is left to the operator although it is preferred that they be adjusted so that about 30 wt. % to about 50 wt. % of the TBHP is converted in the CSTR. Average residence times in the CSTR and the PFR will be adjusted in the manner known to those of ordinary skill in the art, based on the other reaction conditions such as catalyt concentrations, reaction temperatures, etc.

PREPARATION OF PROPYLENE OXIDE FROM PROPYLENE

It has been discovered that under the reaction conditions of the present invention propylene oxide can be produced at high concentrations (24–32%), high selectivities (96–99%) on the basis of t-butyl hydroperoxide converted and high yields (94–98%) of propylene oxide produced on the basis of t-butyl hydroperoxide charged. One particularly preferred set of operating conditions, especially for a continuous process include charging the propylene and hydroperoxide reactants at a low molar ratio of propylene to hydroperoxide (e.g., about 0.5 to about 2 moles of propylene charge per mole of hydroperoxide charge). Another preferred procedure is the use of staged temperatures so that the first 0.5 to 1.5 hours of the reaction are conducted at a lower temperature (50–120° C.) and the second stage also usually an 0.5 to about 1.5 hour reaction time, is conducted at a higher temperature (usually 120–150° C.).

A low molar ratio of propylene to TBHP is further aided by optional staged addition of propylene to a staged plurality of reactors. By this technique, buildup of olefin at any one point in the staged series of reactors, relative to the hydroperoxide, is minimized.

Normally, the charge ratio of propylene to hydroperoxide is thought to be variable over the range of from about 2:1 to 20:1, expressed as a mole ratio. An initial mole ratio of olefin to hydroperoxide of less than 2:1 has been thought to be undesirable because of a loss of selectivity. In this invention, the initial mole ratio of olefin to hydroperoxide of the feed should not exceed 2.0:1. The broad range, expressed in terms of the charge rates of the propylene and the TBHP to a continuously stirred tank reactor is from 0.5:1 to 2.0:1, and preferably from 0.9:1 to 1.8:1. Most preferably, the mole ratio of olefin to hydroperoxide in the feed is 1.05:1 to 1.35:1.

When excess propylene is charged, the ratio of propylene to TBHP in the CSTR will be different from the initial charge ratio because both propylene and TBHP are consumed in the reaction that takes place. In this case, as the TBHP conversion increases, so does the ratio of propylene to TBHP. For example, if the initial molar feed ratio of the charged propylene and TBHP is 1.15 moles of propylene per mole of TBHP, and if the rate of withdrawal of reaction medium from the CSTR is such that about a 50% conversion of the TBHP is maintained in the CSTR, the average mole ratio of unreacted propylene to unreacted TBHP will be about 1.3:1. If the rate of withdrawal of the reaction medium is such that about a 90% conversion of TBHP is maintained in the CSTR, the average mole ratio of unreacted propylene to unreacted TBHP will be about 2.5:1.

In this same situation, and if it be assumed that the TBHP is charged as a 70 wt. % solution of TBHP in tertiary butyl alcohol (TBA), the charge to the CSTR will be composed of about 72.7 wt. % of polar materials (the sum of the weights of TBHP and TBA charged, divided by the sum of the weights of propylene, TBHP and TBA charged.) During the course of the reaction, the propylene (a non-polar material) is converted to propylene oxide (a polar material) so that at the 50% TBHP conversion level mentioned above, the reaction medium will be composed of about 84.6 wt. % of polar materials (the sum of the weights of unreacted TBHP, TBA charged, TBA formed as a reaction product and propylene oxide divided by the said sum of these four materials and unreacted propylene). At the 90% TBHP conversion level mentioned above, the reaction medium will be composed of about 94 wt. % of polar materials on this same basis.

The method and apparatus of this invention are illustrated but not limited by the following examples.

REACTION MEDIUM POLARITY

Example 1

In order to demonstrate the importance of the polarity of the reaction medium in the practice of the process of the present invention, three series of batch runs were made using propylene, propane, tertiary butyl hydroperoxide and tertiary butyl alcohol as feed materials.

In all of the runs, the catalyst that was used was a molybdenum/ethylene glycol complex prepared as follows:

Catalyst Preparation

To a one-liter round-bottomed Morton flask fitted with a mechanical stirrer, a nitrogen inlet, a thermometer, a Dean Stark trap, a condenser and a nitrogen bubbler, were added 100 g. of ammonium heptamolybdate tetrahydrate and 300 g of ethylene glycol. The reaction mixture was heated to 85–110° C. for about 1 hour with nitrogen slowly passing through the flask. At the end of that time, the reaction was essentially complete and essentially all of the ammonium heptamolybdate was dissolved. The reaction mixture was subjected to an aspirator vacuum at a temperature of about 85–95° C. for about 1.5 hours and then reheated to 90–100° C. for an additional hour. On cooling, there was obtained a clear liquid catalyst composition containing 16.1% molybdenum by Atomic Absorption spectroscopy, 1.17% nitrogen (Kjeldahl) and 1.67% water (Karl Fisher analysis).

Epoxidation Runs

The epoxidation runs summarized in Tables 1 and 2 where made in a 300 ml. stainless steel autoclave. The propylene feed component was charged at ambient temperature and then the t-butyl hydroperoxide (TBHP) feed component was charged premixed with 0.38 grams of the catalyst. This provided for a catalyst concentration of about 350 ppm of catalyst in the reaction medium. For the pure propylene runs, the TBHP feed component consisted of about a 72.36 wt. % solution of TBHP in t-butyl alcohol which contained about 0.2 wt. % of water. For the Propylene/Propane runs wherein propane was added to the propylene feed component and for the Propylene/TBA runs wherein additional t-butyl alcohol was added to the TBHP feed component, the TBHP feed component consisted of a 73.0 wt. % solution of TBHP in t-butyl alcohol that contained about 0.2 wt. % of water. The quantities of feed component were adjusted for each of the runs in order to provide the desired mole ratio of propylene to TBHP shown in Tables 1 and 2.

Thus, by way of example, in Run No. 1 of Table 1, the propylene feed component consisted of about 49.4 grams of propylene and the TBHP feed component consisted of about 93.36 g. of TBHP, about 35.4 g. of t-butyl alcohol, about 0.26 gram of water and about 0.38 gram of catalyst.

In Run No. 2 of Table 1, the propylene feed component consisted of about 34.65 grams of propylene and about 35.45 grams of propane. The TBHP feed component consisted of about 71.72 grams of TBHP, about 26.33 g. of t-butyl alcohol, about 0.2 g. of water and about 0.38 g. of catalyst.

In Run No. 3 of Table 1, the propylene feed component consisted of about 36.4 g. of propylene and the TBHP feed component consisted of about 74.36 g. of TBHP, about 64.27 g. of t-butyl alcohol, about 0.2 g. of water and about 0.38 g. of catalyst.

All of the runs reported in Table 1 were conducted at 120° C. for about 2.0 hrs. All of the runs reported in Table 2 were conducted at 110° C. for 1.0 hour and 130° C. for 1.0 hour.

The reactants employed and the results obtained are reported in Tables 1 and 2.

TABLE 1

| Column | 1 | 2 | 3 | 4 | 5 | 6 | 7 | 8 | 9 |
|---|---|---|---|---|---|---|---|---|---|
| Run No. | Olefin Feed | Mole Ratio Propylene/ TBHP | Wt. % PO Total Eff. | PO Sel. Basis TBHP % | TBHP Conv. % | Moly Bal. % | Σ All Unks. After PG | ppm $C_3=$ dimer Basis Pure PO | wt. % Polar Species Basis Total Charge |
| 1 | Propane/Propylene Mixture[1] | 1.03 | 22.0 | 88.9 | 90.8 | 83.0 | 0.63 | 4 | 58.2 |
| 2 | Pure Propylene | 1.01 | 30.6 | 92.5 | 95.5 | 119.8 | 1.12 | 3 | 74.6 |
| 3 | Pure Propylene, TBA Added[2] | 0.96 | 22.2 | 92.2 | 87.0 | 89.2 | 0.50 | 1 | 80.6 |
| 4 | Propane/Propylene Mixture[1] | 1.15 | 21.9 | 90.8 | 92.8 | 85.1 | 0.71 | 6 | 55.5 |
| 5 | Pure Propylene | 1.13 | 30.4 | 94.2 | 95.9 | 105.3 | 0.99 | 4 | 72.4 |
| 6 | Pure Propylene, TBA Added[2] | 1.17 | 23.1 | 95.0 | 94.2 | 93.6 | 0.56 | 3 | 78.1 |
| 7 | Propane/Propylene Mixture[1] | 1.35 | 21.1 | 91.3 | 95.6 | 82.7 | 0.40 | 11 | 51.6 |
| 8 | Pure Propylene | 1.31 | 30.4 | 96.0 | 98.3 | 102.5 | 0.68 | 11 | 69.3 |
| 9 | Pure Propylene, TBA Added[2] | 1.31 | 22.2 | 95.2 | 95.5 | 102.6 | 0.54 | 5 | 76.7 |
| 10 | Propane/Propylene Mixture[1] | 1.61 | 19.5 | 91.6 | 96.6 | 76.5 | 0.65 | 18 | 47.2 |
| 11 | Pure Propylene | 1.59 | 28.8 | 97.1 | 98.2 | 103.5 | 0.74 | 43 | 65.0 |
| 12 | Pure Propylene, TBA Added[2] | 1.63 | 20.9 | 97.4 | 98.1 | 91.4 | 0.53 | 27 | 74.0 |
| 13 | Propane/Propylene Mixture[1] | 2.08 | 17.5 | 94.1 | 97.2 | 70.5 | 0.45 | 40 | 40.9 |
| 14 | Pure Propylene | 2.10 | 25.8 | 94.6 | 99.9 | 111.2 | 0.82 | 71 | 58.3 |
| 15 | Pure Propylene, TBA Added[2] | 1.89 | 18.6 | 95.9 | 98.0 | 89.7 | 0.70 | 35 | 72.8 |
| 16 | Propane/Propylene Mixture[1] | 3.04 | 14.0 | 94.8 | 98.4 | 77.5 | 0.45 | 135 | 32.2 |
| 17 | Pure Propylene | 2.71 | 22.8 | 94.9 | 99.0 | 100.9 | 0.60 | 84 | 52.2 |
| 18 | Pure Propylene | 3.32 | 21.1 | 96.8 | 99.8 | 95.8 | 0.52 | 86 | 47.1 |
| 19 | Pure Propylene, TBA Added[2] | 2.99 | 14.6 | 97.4 | 99.2 | 94.6 | 0.41 | 76 | 67.1 |

TABLE 1-continued

| Column | 1 | 2 | 3 | 4 | 5 | 6 | 7 | 8 | 9 |
|---|---|---|---|---|---|---|---|---|---|
| Run No. | Olefin Feed | Mole Ratio Propylene/ TBHP | Wt. % PO Total Eff. | PO Sel. Basis TBHP % | TBHP Conv. % | Moly Bal. % | Σ All Unks. After PG | ppm C₃= dimer Basis Pure PO | wt. % Polar Species Basis Total Charge |
| 20 | Propane/Propylene Mixture[1] | 5.34 | 9.3 | 94.0 | 98.7 | 69.7 | 0.09 | 344 | 21.5 |
| 21 | Pure Propylene, TBA Added[2] | 5.19 | 9.7 | 94.4 | 98.6 | 76.1 | 0.14 | 206 | 61.1 |

The above runs were conducted at 120° C. reaction temperature and 2.0 hour reaction time. The catalyst used was made from EG and AHM and was present at the 350 ppm level basis total charge. The TBHP concentration was 72%.
[1]Propane/Propylene Mixture 1/1 Mole Ratio
[2]TBA added to TBHP solution in an amount equal to the propane added in the corresponding propane/propylene run.

TABLE 2

| Column | 1 | 2 | 3 | 4 | 5 | 6 | 7 | 8 | 9 |
|---|---|---|---|---|---|---|---|---|---|
| Run No. | Olefin Feed | Mole Ratio Propylene/ TBHP | Wt. % PO Total Eff. | PO Sel. Basis TBHP % | TBHP Conv. % | Moly Bal. % | Σ All Unks. After PG | ppm C₃= dimer Basis Pure PO | wt. % Polar Species Basis Total Charge |
| 22 | Propane/Propylene Mixture[1] | 1.03 | 21.2 | 81.6 | 94.9 | 122.9 | 1.28 | 9 | 58.4 |
| 23 | Pure Propylene | 1.02 | 29.6 | 91.8 | 93.0 | 93.8 | 1.12 | <1 | 74.5 |
| 24 | Pure Propylene, TBA Added[2] | 1.05 | 23.1 | 89.7 | 94.3 | 90.8 | 0.54 | 4 | 79.3 |
| 25 | Propane/Propylene Mixture[1] | 1.21 | 21.5 | 86.3 | 97.4 | 107.2 | 1.08 | 19 | 54.7 |
| 26 | Pure Propylene | 1.17 | 30.4 | 93.6 | 97.4 | 99.9 | 0.74 | 9 | 71.6 |
| 27 | Pure Propylene, TBA Added[2] | 1.16 | 23.4 | 93.8 | 96.1 | 76.8 | 0.75 | 7 | 78.2 |
| 28 | Propane/Propylene Mixture[1] | 1.33 | 20.7 | 86.6 | 97.6 | 87.6 | 1.00 | 29 | 52.2 |
| 29 | Pure Propylene | 1.29 | 30.2 | 94.9 | 98.4 | 93.8 | 0.86 | 45 | 69.6 |
| 30 | Pure Propylene, TBA Added[2] | 1.36 | 22.6 | 94.7 | 98.0 | 96.2 | 0.74 | 18 | 76.0 |

The above runs were conducted at 110° C. for 1.0 hour followed by 1.0 hour at 130° C. The catalyst used was made from EG and AHM and was present at the 350 ppm level basis total charge. The TBHP concentration was 72%.
[1]Propane/Propylene Mixture 1/1 Mole Ratio
[2]TBA added to TBHP solution in an amount equal to the propane added in the corresponding propane/ propylene run.

Turning first to Table 1, it will be noted that the runs have been arranged in "triplets", based on the mole ratio of propylene to TBHP, with each set of "triplets" having a progressively increasing mole ratio of propylene to TBHP. With reference to Column 4, reporting the results obtained in terms of propylene oxide selectivity, based on TBHP, it will be noted that when the polarity of the charge was reduced in Run No. 1 through the addition of a mole of propane, so that the polar components of the charge (TBHP and TBA) constituted only about 58.2 wt. % of the charge, there was a significant loss of selectivity, as compared with Run No. 2 of the present invention where the polar components of the charge constituted about 74.6 wt. %. Run No. 3 wherein the polarity of the charge was increased through the use of an equivalent amount of additional TBA, based on the amount of propane used in Run No. 1, so the polar components of the charge constituted about 80.6 wt. % of the charge demonstrates that the poor selectivity of Run No. 1 was due to a reduction in the polarity of the charge rather than a "dilution" of the reactants. Run 3 had the same "dilution" relative to Run 2, as did Run 1.

The same effect on propylene oxide selectivity basis TBHP reacted is noted in the second, third and fourth set of data "triplets" (Runs 4-12).

For the fifth set of triplets (Runs 13-15), it can be calculated that only 40.9 wt. % of the charge components were polar for Run No. 13 and that only 58.3 wt. % of the charge components were polar for Run No. 14, but essentially equivalent results were obtained. As shown by Run No. 15, increasing the percentage of polar components in the charge to 72.8 wt. % only marginally improved the selectivity of the TBHP to propylene oxide. At higher initial propylene to TBHP ratios (1.9-2.1 to 1) the effect of polar media stabilization of TBHP and catalyst is "washed-out" by the increased rates of reaction (less TBHP) product by increased propylene concentration. The penalty for increased propylene concentration is increased propylene dimer make as evidenced by results in column 8.

In the next set of data (Runs 16-19), the polar components constituted about 32.2 wt. %, 52.2 wt. %, and 47.1 wt. % in runs 16-18. Essentially equivalent results were obtained. There was no improvement in the selectivity of the TBHP to propylene oxide in Run No. 19 when the polar components constituted about 67.1 wt. % of the charge. Note from Column 8, however, that there was a further significant increase in the amount of propylene dimer that was formed at the higher mole ratios of propylene to TBHP of Runs 16-21 which are outside the scope of the present invention. In runs 16-21 the selectivities of TBHP to propylene oxide were essentially equal because of the "wash" carried by sharply increased reaction rates (less TBHP decomposition because of increased propylene to TBHP mole ratios).

Turning next to Table 2, it will be seen that the pattern is repeated, in Runs 22, 25 and 28 when the polar components constituted 58.4 wt. %, 54.7 wt. % and 52.2 wt. %, respectively, of the charge components, the selectivity to the TBHP to propylene oxide (Column 4) was significantly less than the selectivity obtained in Runs 23, 26 and 27 of the present invention where the polar components constituted 74.5 wt. %, 71.6 wt. % and 69.6 wt. %, respectively, of the charge. The selectivities of Runs 22, 25 and 28 were also significantly less than the selectivities obtained in Runs 24, 27 and 30 where the polar components constituted 79.3 wt. %, 78.2 wt. % and 76.0 wt. %, respectively of the charge.

Example 2

Examples 2-4 show the importance of relatively high catalyst concentrations on the yields, selectivities, and conversions when the epoxidations are conducted at low reaction temperatures.

To a 300 ml 316 stainless steel autoclave (purged with nitrogen) was added 43.9 g (1.0452 moles) of propylene at room temperature. Also at room temperature was added a premixed solution of 88.2 g of TBHP (consisting of 60.75% TBHA, 38.91% TBA and 0.34% water) and 0.9 g of molybdenum 2-ethyl-1-hexanol (5.96% molybdenum) catalyst. The molybdenum 2-ethyl-1-hexanol catalyst was made by heating 29.0 g of molybdenum trioxide with 299.5 g 2-ethyl-1-hexanol and 20 ml concentrated NH₄OH and 250 ml toluene from room temperature to 140° C. over a 1¾ hour period removing about 9 ml water and 165 ml toluene. The heating continued from 140° C. to 153° C. for another 4.25 hours at which point about 16 ml water and 234 ml toluene had been recovered. The reaction mixture was filtered and the filtrate appeared to contain water so it was dried over molecular sieves. The dried material was refiltered and analyzed for molybdenum and found to contain 5.96% molybdenum. This was the 0.9 g of catalyst that was premixed with the TBHP solution and charged to the autoclave at room temperature after the propylene was added. The mole ratio of propylene/TBHP in this run was 1.75:1 and TBHP/TBA was 1.28:1 and the catalyst level was 0.0403 wt. % molybdenum basis total reactor charge. The autoclave was heated with stirring to 110° C. over a 30 minute period and held at 110° C. for 90 minutes. The reaction mixture was cooled to room temperature and sampled under pressure. The total weight of the product recovered was 133.0 g and the total weight of the liquid product (after propylene was stripped) was 93.0 g.

The liquid product was analyzed and found to contain 1.18% TBHP.

Grams of TBHP remaining = 1.0974 g moles of TBHP remaining = 0.0122 moles TBHP reacted = moles fed − moles remaining moles TBHP reacted = 0.5954 − 0.0122 = 0.5832

$$\text{Conversion TBHP} = \frac{\text{moles reacted}}{\text{moles fed}} = \frac{0.5832}{0.5954} = 97.94\%$$

The total product analyzed under pressure was found to contain 24.729 wt. % propylene oxide and 0.152 wt. % propylene glycol. It should further be noted that the total product contains only 13.922% propylene unreacted.

Grams propylene oxide = 32.8896 g moles PO = 0.5671

$$\text{Selectivity to PO} = \frac{\text{moles PO}}{\text{moles TBHP reacted}} = \frac{0.5671}{0.5832} = 97.23\%$$

$$\text{Yield of PO} = \frac{\text{moles PO}}{\text{moles TBHP fed}} = \frac{0.5671}{0.5954} = 95.24\%$$

The same liquid product was also analyzed by atomic absorption spectroscopy and found to contain 526 ppm molybdenum, or a 91.5% molybdenum recovery.

Example 3

To a 300 ml 316 stainless steel autoclave (purged with nitrogen) was added 45.3 g (1.07857 moles) of propylene. Also at room temperature was added a premixed solution of 88.15 g of TBHP (consisting of 60.75% TBHP, 38.91% TBA, and 0.34% water) and 0.45 g of molybdenum 2-ethyl-1-hexanol catalyst (5.96% molybdenum) whose preparation was described in Example 2. In this epoxidation the mole ratio of propylene to TBHP was 1.81:1 and the mole ratio of TBHP/TBA was 1.28:1 and the amount of moly catalyst was 0.0200 wt. % basis total reactor charge. The amount of catalyst used here is about half that used in Example 2. Here again the low propylene to TBHP ratio leads to sharply increased molybdenum recoveries.

The autoclave was heated with stirring to 110° C. over a 30 minute period and held at 110° C. for 90 minutes. The reaction mixture was cooled to room temperature and sampled under pressure. The total weight of the product recovered was 133.9 g and the weight of the liquid product (after propylene was stripped) was 94.2 g. The liquid product was analyzed and contained 264 ppm molybdenum or a 93.0% molybdenum recovery.

The liquid product was analyzed and found to still contain 3.92% TBHP.

Grams of TBHP remaining = 94.2 × 3.92% = 3.69264 g moles TBHP remaining = 0.0410 moles moles TBHP reacted = moles fed − moles remaining moles TBHP reacted = 0.5950 − 0.0410 0.5540

$$\text{Conversion TBHP} = \frac{\text{moles reacted}}{\text{moles fed}} = \frac{0.5540}{0.5950} = 93.11\%$$

The total product analyzed under pressure was found to contain 22.928 wt. % propylene oxide and 16.14% unreacted propylene.

grams propylene oxide = 133.9 × 22.928% = 30.70 g moles propylene oxide = 0.5293 moles $$\text{Selectivity to PO} = \frac{\text{moles PO}}{\text{moles TBHP reacted}} = \frac{0.5293}{0.5540} = 95.54\%$$

$$\text{Yield PO} = \frac{\text{moles PO}}{\text{moles TBHP fed}} = \frac{0.5293}{0.5950} = 88.96\%$$

In essentially identical runs, except that the catalyst concentration was reduced in Example 3, the yield of propylene oxide was some 6% lower than in Example 2 with the higher catalyst concentration. Note, however, that the molybdenum recovery (soluble molybdenum) in the reactor effluent in Example 3 was very high (93.0%) and even higher than in Example 2 (91.5%).

Example 4

To a nitrogen purged 300 ml 316 stainless steel autoclave was added 48.3 g (1.1500 moles) of propylene at room temperature. To the propylene was added a premixed solution of TBHP (124.2 g) and molybdenum catalyst (1.2 g). The TBHP part of the premixed TBHP/molybdenum catalyst solution consisted of 124.2 g having the following composition: 60.50% TBHP, 39.30% TBA and 0.2% water. The molybdenum catalyst part of the premixed TBHP/molybdenum catalyst solution consisted of 1.2 g of the molybdenum 2-ethyl-1-hexanol (6.50% molybdenum content) catalyst.

The concentrated molybdenum catalyst was prepared by mixing 299.5 g 2-ethyl-1-hexanol with 29.0 g MoO₃ and to this mixture was added 20 ml of concentrated ammonium hydroxide. The catalyst preparation reaction mixture was heated to 180° C. and held there for five hours removing some 21 ml of water. The reaction mixture was cooled and filtered. Atomic absorption analysis indicated the molybdenum content of the filtrate was 6.50% (97.7% molybdenum incorporated into soluble catalyst form).

In this reaction the propylene to TBHP mole ratio was only 1.38:1 and the mole ratio of TBHP/TBA was 1.27:1. The amount of molybdenum catalyst used was 0.0449 wt. % molybdenum basis total reactor charge. The autoclave and contents were heated to 110° C. with stirring for 120 minutes (2.0 hours). The reaction mixture was cooled and pressured out into two sample bombs.

The total product weight was 173.5 g
The total weight of liquid product was 142.2 g
The liquid product was examined and found to contain 1.70% TBHP.

grams TBHP remaining = 2.4174 g
moles TBHP remaining = 0.026 g
moles TBHP reacted = moles fed − moles remaining
moles TBHP reacted = 0.8349 − 0.0269
moles TBHP reacted = 0.8080

Conversion = $\frac{0.8080}{0.8349}$ = 96.78%

The liquid product was analyzed by atomic absorption spectroscopy and found to contain 527 ppm molybdenum, which is essentially a 96.1% recovery of molybdenum.

Examples 5 And 6

Examples 5 and 6 were conducted similarly to Examples 2-4, except that different molybdenum 2-ethyl hexanol catalysts were utilized. The results, however, are essentially similar, very high recoveries of soluble molybdenum at the end of the reaction (96.0% in both runs). These results are summarized in brief tabular form below. The runs were conducted at 110° C. for 1.5 hours.

When research into this area was first begun, it was discovered that results improved dramatically when dry TBHP (less than 0.4 wt. % $H_2O$) was used instead of the commercially available TBHP. Therefore, it is preferred that the TBHP/TBA solutions contain very little water, 0.5 wt. % or less. In our initial propylene epoxidation experiments, high olefin/hydroperoxide mole ratios were chosen because of the repeated mention in patents and the literature that selectivities are lower when propylene/TBHP mole ratios are low. Over 130 epoxidation runs were conducted at propylene/ TBHP moles ratios of 6:1-10:1. At these ratios various catalysts and changes in conditions seemed to have no large effect on epoxidation results. Further, the molybdenum recoveries at 6-10:1 ratios were in the 60-80% range.

However, when low initial propylene/TBHP mole ratios were used in an attempt to find a method which would help differentiate between the many molybdenum catalysts being synthesized, it was surprisingly discovered that the propylene oxide selectivities were excellent, provided that reaction temperatures, residence times, and molybdenum catalyst concentrations were adjusted properly.

It has been further discovered that enhancement of the results is achieved when the epoxidation reaction is conducted at comparatively low reaction temperature using comparatively high concentrations of molybdenum catalyst. In addition, it has been also surprisingly discovered that a high proportion of the molybdenum charged emerged as soluble molybdenum and this proportion increased upon reduction of the propylene/TBHP charge ratio. Further, it was found that low ratios of propylene to TBHP in the charge lead to low by-product propylene dimer make.

Table 4 gives data about the concentration of propylene dimer in reactor effluents. Propylene dimer was determined in reactor effluents using a GC-mass spectrometer. Propylene dimer, as noted, is an objectionable by-product because it co-distills with propylene oxide and is best separated from propylene oxide by a costly extractive distillation. The cost of the extractive distillation towers as well as the utilities cost to operate such a purification unit is very high. The examples of Table 5 where the conventional propylene oxide process conditions are used reveals that the propylene dimer levels seen in Table 4 are surprisingly low.

Table 5 presents examples where results are improved even further with high TBHP concentrations together with low propylene/TBHP mole ratios, reaction staging and lower catalyst levels. These examples represent the preferred reaction conditions and at 1.1-1.2:1 propylene/TBHP mole ratios. The examples of Table 6 show that the molybdenum catalyst may be recycled with good results.

Examples 21 through 25 of Table 7 show the results obtained when the inventive process was scaled up 3.3 fold to a 1000 ml reactor. The only procedural difference in these examples was that after the propylene was charged to the reactor, it was heated up to, at or near

TABLE 3

| Ex. | Wt % moly charged | Propylene/ TBHP mole ratio | PO Wt. % | PO Yield | PO Sel. | Conv. | ppm moly in Liquid | % moly Recovery |
|---|---|---|---|---|---|---|---|---|
| 4 | 0.0402 | 1.79:1 | 24.71 | 95.65 | 98.25 | 97.35 | 506 | 96.0 |
| 5 | 0.0393 | 1.82:1 | 25.28 | 97.57 | 99.86 | 97.71 | 498 | 96.0 | the reaction temperature before the TBHP/TBA/catalyst solution was added. Exotherm was allowed to carry the reaction to the desired temperature. Even at these quantities, excellent results are maintained.

Table 5A gives typical catalyst preparations involving 2-ethyl-1-hexanol and ammonium heptamolybdate.

Table 8 presents examples which demonstrate that the reaction can proceed successfully with a two-part reactor scheme. A CSTR is followed by a PFR at a slightly higher temperature. Low propylene/TBHP ratios are again demonstrated. Catalyst recoveries are sometimes reported as slightly greater than 100%. The excess should be taken as experimental error, and the recovery taken as essentially quantitative.

The inventive process provides high concentrations of propylene oxide (24-32%) and utilizes much less propylene due to the lower propylene/TBHP mole ratio and polar reaction media. In this process, 4 to 16% of the propylene is unreacted. Our selectivities (moles of propylene oxide formed per mole of TBHP consumed) do not drop as we lower the propylene/TBHP mole ratio. Surprisingly, increased selectivities to propylene oxide basis TBHP are observed. This is because the media is more polar.

It is surprising that selectivities to the alkylene oxide are at least 96%, concentrations of the alkylene oxide in the product stream can be at least 24%, yields to the alkylene oxide are at least 94% and hydroperoxide conversions are at least 96%, all simultaneously, using the method of this invention. Further, it is surprising that molybdenum recoveries at the lower ratios of propylene/TBHP generally are >90%.

TABLE 4

EXAMPLES USING LOW TEMPERATURES AND LOW REACTANT RATIOS TO GIVE LOW DIMER BY-PRODUCT PROPORTION

| Example | Cat. Con. Wt. % Moly Basis Total Reaction Charge | Reaction Temp., °C. | Reaction Time, Hours | Propylene/ TBHP Mole Ratio | Propylene Oxide, wt. % | ppm $C_3$ dimer, pure PO basis (GC Mass Spec) | Propylene Oxide Yield | Propylene Oxide Selectivity | TBHP Conv. | Molybdenum Catalyst Recovery, % |
|---|---|---|---|---|---|---|---|---|---|---|
| 5[1] | 0.0402 | 110 | 1.5 | 1.79 | 24.71 | 20 | 95.65 | 98.25 | 97.35 | 96.0 |
| 6[2] | 0.0393 | 110 | 1.5 | 1.82 | 25.28 | 20 | 97.57 | 99.86 | 97.71 | 96.0 |
| 2[3] | 0.0403 | 110 | 1.5 | 1.75 | 24.73 | 20 | 95.24 | 97.24 | 97.95 | 91.2 |
| 3[3] | 0.0200 | 110 | 1.5 | 1.81 | 22.93 | 22 | 88.96 | 95.54 | 93.10 | 92.7 |

[1]Catalyst was $MoO_3$/2-ethylhexanol/$NH_4OH$ complex (3.3% molybdenum).
[2]Catalyst was $MoO_3$/2-ethylhexanol/$NH_4OH$/toluene complex (5.86% molybdenum).
[3]Catalyst was $MoO_3$/2-ethylhexanol/$NH_4OH$/toluene complex (5.96% molybdenum).

TABLE 5

COMPARATIVE EXAMPLES USING CONVENTIONAL PARAMETERS

| Example | Cat. Con. Wt. % Moly Basis Total Reaction Charge | Reaction Temp., °C. | Reaction Time, Hours | Propylene/ TBHP Mole Ratio | Propylene Oxide, wt. % | ppm $C_3$ dimer, pure PO Basic (GC Mass Spec) | Propylene Oxide Yield | Propylene Oxide Selectivity | TBHP Conv. | Molybdenum Catalyst Recovery, % |
|---|---|---|---|---|---|---|---|---|---|---|
| 7[1] | 0.0058 | 120 | 1.0 | 5.90 | 12.76 | 118 | 85.65 | 97.93 | 87.46 | 46.0 |
| 8[1] | 0.0220 | 120 | 1.0 | 5.80 | 14.36 | 174 | 96.97 | 98.41 | 98.53 | 93.6 |
| 9[1] | 0.0064 | 135 | 1.0 | 5.80 | 13.65 | 403 | 91.36 | 94.01 | 97.18 | 68.6 |
| 10[1] | 0.0226 | 135 | 1.0 | 5.54 | 14.55 | 1203 | 95.15 | 96.59 | 98.51 | 73.5 |
| 11[2] | 0.0132 | 120 | 1.0 | 6.27 | 13.99 | 286 | 98.70 | 100.26 | 98.45 | 77.2 |
| 12[2] | 0.0133 | 135 | 1.0 | 6.23 | 14.66 | 1194 | 102.83 | 104.61 | 98.31 | 66.2 |

EXAMPLES OF RUNS USING LOW PROPYLENE/TBHP RATIOS, HIGH TBHP CONCENTRATIONS, STAGED TEMPERATURES AND LOWER CATALYST LEVELS

| Example | Cat. Con. Wt. % Moly Basis Total Reaction Charge | TBHP, wt. % | Reaction Temp., °C. | Reaction time, Hours | Propylene/ TBHP Mole Ratio | Propylene Oxide, wt. % | ppm $C_3$ dimer, pure PO basis (GC Mass Spec) | Propylene Oxide Yield | Propylene Oxide Selectivity | TBHP Conv. | Molybdenum Catalyst Recovery, % |
|---|---|---|---|---|---|---|---|---|---|---|---|
| 13 | 0.0256 | 72.6 | 110/135 | 1.0/1.0 | 1.12 | 31.56 | 16 | 93.37 | 96.14 | 97.12 | 94.1 |
| 14 | 0.0251 | 72.6 | 110/136 | 1.0/1.0 | 1.14 | 31.79 | 10 | 94.48 | 98.11 | 96.30 | 96.3 |
| 15 | 0.0198 | 72.6 | 110/141 | 1.0/1.0 | 1.14 | 31.18 | 13 | 92.68 | 96.91 | 95.63 | 93.7 |

NOTE: For a description of each catalyst used in each of the above runs and how it was prepared, see Table 5.
[1]Catalyst was $MoO_3$/2-ethylhexanol/$NH_4OH$ complex (6.50% molybdenum; same as catalyst prepared in Example 4).
[2]Catalyst was AHM/2-ethylhexanoic acid (5.97% molybdenum, acid no. of 292).

TABLE 5A

| From Table 5 Example(s) No. in Which Catalyst was Used | Reaction Time, Hours | 2-Ethyl-1-hexanol, grams | Ammonium Hepta-molybdate, grams | Water, grams | Ratio Alcohol/g atoms Molybdenum | Ratio Water/g atoms Molybdenum | Molybdenum in Catalyst, % | Molybdenum Incorporated, % | Days Catalyst Stayed Clear |
|---|---|---|---|---|---|---|---|---|---|
| 13 | 8.0 | 182.32 | 35.31 | 7.2 | 7.0:1 | 2:1 | 9.79 | 92.20 | 60 |
| 14 | 8.0 | 200.0 | 31.90 | 6.5 | 8.5:1 | 2.0:1 | 8.33 | 94.67 | 35 |
| 15 | 3.0 | 299.5 | 35.50 | 7.2 | 11.4:1 | 2.0:1 | 6.31 | 100.78 | 30 |

TABLE 6

EXAMPLES USING RECYCLED CATALYST

| Example | Cat. Con. Wt. % Moly Basis Total Reaction Charge | TBHP, wt. % | Reaction Temp., °C. | Reaction Time, Hours | Propylene/ TBHP Mole Ratio | Propylene Oxide, wt. % | ppm $C_3$ dimer, pure PO basis (GC Mass Spec) | Propylene Oxide Yield | Propylene Oxide Selectivity | TBHP Conv. | Molybdenum Catalyst Recovery, % |
|---|---|---|---|---|---|---|---|---|---|---|---|
| 16[1] | 0.0399 | 69.6 | 110 | 1.5 | 1.63 | 28.11 | 18 | 96.19 | 98.86 | 97.30 | 93.0 |
| 17[2] | 0.0397 | 69.6 | 112 | 1.5 | 1.64 | 27.71 | 14 | 95.49 | 99.35 | 96.12 | 85.2 |
| 18[3] | 0.0395 | 69.6 | 110 | 1.5 | 1.64 | 28.09 | 11 | 97.31 | 101.72 | 95.67 | 102.6 |
| 19[4] | 0.0391 | 69.6 | 110 | 1.5 | 1.65 | 27.60 | 15 | 96.38 | 100.10 | 96.28 | 115.6 |

TABLE 6-continued
EXAMPLES USING RECYCLED CATALYST

| Example | Cat. Con. Wt. % Moly Basis Total Reaction Charge | TBHP, wt. % | Reaction Temp., °C. | Reaction Time, Hours | Propylene/ TBHP Mole Ratio | Propylene Oxide, wt. % | ppm $C_3$ dimer, pure PO basis (GC Mass Spec) | Propylene Oxide Yield | Propylene Oxide Selectivity | TBHP Conv. | Molybdenum Catalyst Recovery, % |
|---|---|---|---|---|---|---|---|---|---|---|---|
| 20[4] | 0.0481 | 69.6 | 110 | 1.5 | 1.61 | 27.72 | 18 | 96.33 | 100.75 | 95.61 | 103.0 |

[1]Catalyst was 100% AHM/2-ethylhexanol/$H_2O$ complex (4.5% molybdenum).
[2]Catalyst was ⅔ that used in Example 16 and ⅓ of a similar once used recycled catalyst (1.6% molybdenum).
[3]Same catalyst as Example 17 except proportion is reversed; ⅓ that used in Ex. 16 and ⅔ once used recycled catalyst.
[4]Catalyst was 100% once-used recycled catalyst (1.6% molybdenum).

TABLE 7
EXAMPLES SCALED UP 3.3 FOLD

| Example | Cat. Con. Wt. % Moly Basis Total Reaction Charge | TBHP, wt. % | Reaction Temp., °C. | Reaction Time, Hours | Propylene/ TBHP Mole Ratio | Propylene Oxide, wt. % | ppm $C_3$ dimer, pure PO basis (GC Mass Spec) | Propylene Oxide Yield | Propylene Oxide Selectivity | TBHP Conv. | Molybdenum Catalyst Recovery, % |
|---|---|---|---|---|---|---|---|---|---|---|---|
| 21[1] | 0.0450 | 68.57 | 110 | 1.0 | 1.79 | 26.64 | 11 | 95.27 | 99.09 | 96.14 | 107.7 |
| 22[2] | 0.0449 | 68.57 | 95 | 1.5 | 1.79 | 26.46 | 8 | 94.07 | 99.55 | 94.50 | 107.5 |
| 23[3] | 0.0531 | 68.57 | 110 | 1.5 | 1.49 | 28.79 | 12 | 96.05 | 98.83 | 97.19 | 102.1 |
| 24[2] | 0.0450 | 68.57 | 125* | 1.5 | 1.79 | 27.82 | 90 | 98.84 | 99.21 | 99.63 | 110.0 |
| 25[2] | 0.0450 | 68.57 | 110 | 2.0 | 1.79 | 27.71 | 14 | 98.53 | 99.26 | 99.27 | 96.8 |

*The reaction temperature exothermed to 136° C.
[1]Catalyst was AHM/2-ethylhexanol/$H_2O$ complex (3.87% molybdenum).
[2]Catalyst was AHM/2-ethylhexanol/$H_2O$ complex (6.16% molybdenum).
[3]Catalyst was AHM/2-ethylhexanol complex (7.33% molybdenum).

TABLE 8
EXAMPLES USING TWO-STEP REACTOR SCHEME AND VERY LOW PROPYLENE:TBHP MOLE RATIO
1 Hour in CSTR Followed by 1 Hour in a Plug Flow Reactor, TBHP wt. % always 68.05

| Example No. | Cat. Con. Wt. % Moly Basis Total Reaction Charge | CSTR Reaction Temp., °C. | PFR Reaction Temp., °C. | Propylene/ TBHP Mole Ratio | Propylene Oxide, wt. % | ppm $C_3$ dimer, pure PO basis (GLC/MSD) | Propylene Oxide Yield | Propylene Oxide Selectivity | TBHP Conv. | Molybdenum Catalyst Recovery, % |
|---|---|---|---|---|---|---|---|---|---|---|
| 26 | 0.0518 | 110 | 120 | 1.34 | 31.60 | 10 | 98.59 | 101.06 | 97.56 | 89.6 |
| 27 | 0.0516 | 110 | 130 | 1.09 | 32.20 | 3 | 95.25 | 98.74 | 96.47 | 86.7 |
| 28 | 0.0512 | 110 | 130 | 1.05 | 31.82 | 0 | 93.15 | 100.03 | 93.12 | 88.0 |
| 29 | 0.0512 | 110 | 135 | 1.22 | 31.95 | 16 | 97.40 | 99.76 | 97.63 | 76.8 |
| 30 | 0.0516 | 110 | 134 | 1.30 | 31.46 | 64 | 97.95 | 99.26 | 98.26 | 83.7 |
| 31 | 0.0503 | 110 | 135 | 1.18 | 31.63 | 0 | 95.94 | 97.78 | 98.12 | 96.9 |

Hydroperoxide Choice

Representative runs were made to demonstrate that t-amyl hydroperoxide may also be used in the practice of the present invention.

Example 32

Catalyst Preparation

To a one-liter round-bottomed Morton flask fitted with a mechanical stirrer, a nitrogen inlet, a thermometer, a Dean Stark trap, a condenser and a nitrogen bubbler, were added 100 g. of either ammonium heptamolybdate (Catalyst A) or ammonium dimolybdate (Catalyst B) and 300 g of ethylene glycol. The reaction mixture was heated to 85–110° C. for about 1 hour with nitrogen slowly passing through the flask. At the end of that time, the reaction was essentially complete and essentially all of the ammonium molybdate was dissolved. The reaction mixture was subjected to an aspirator vacuum at a temperature of about 85–95° C. for about 1.5 hours and then reheated to 90–100° C. for an additional hour. On cooling, there was obtained a clear liquid catalyst composition containing (Catalyst A) 16.1% molybdenum by Atomic Absorption spectroscopy, 1.17% nitrogen (Kjeldahl) and 1.67% water (Karl Fisher analysis). The acid number of the catalyst (mg KOH per gram of sample) was found to be 80.94 and 167.85 in duplicate analyses and (Catalyst B) 13.2% molybdenum by Atomic Absorption spectroscopy.

Epoxidation Runs

The epoxidation runs summarized in Table 9 where made in a 300 ml. stainless steel autoclave. The propylene feed component was charged at ambient temperature and then the t-amyl hydroperoxide (TAHP) feed component was charged premixed with 0.38 grams of the catalyst. This provided for a catalyst concentration of about 350 ppm of catalyst in the reaction medium. The TAHP feed component consisted of about a 70 wt. % solution of TAHP in t-amyl alcohol (TAA) which contained about 0.2 wt. % of water. The reaction conditions employed and the results obtained are summarized in Table 9.

TABLE 9

T—AMYL HYDROPEROXIDE*

| NB# | Rxn Temp °C. | Rxn Time Hrs. | Catalyst Used | wt. % Moly Basis Total Reactor Charge | Propylene to TAHP Mole Ratio | Propylene Oxide Conc. wt. % | Propylene Oxide Selectivity (Basis TAHP Reacted) | TAHP Conversion moles TAHP Reacted/Moles TAHP Feed | wt. % TAHP Remaining Unreacted | Molybdenum Recovery |
|---|---|---|---|---|---|---|---|---|---|---|
| 6060-97 | 120 | 2.0 | A | 0.0350 | 1.16/1 | 28.74 | 97.73 | 94.67 | 3.43 | Q |
| 6060-98 | 120 | 2.0 | B | 0.0311 | 1.15/1 | 28.88 | 96.62 | 95.97 | 2.47 | Q |

A = Moly-EG complex made from ethylene glycol and ammonium heptamolybdate (% moly = 16.1%)
B = Moly-EG complex made from ethylene glycol and ammonium dimolybdate (% moly = 13.2%)
Q = Quantitative (soluble molybdenum recovered was essentially equal to the amount charged)
*Obtained from Lucidol and dried thoroughly over 4A molecular sieves.
t-amyl hydroperoxide = 75.59% (wt. %)
t-amyl alcohol = 23.98% (wt. %)
$H_2O$ = 0.43% (wt. %)

From Table 9 it will be seen that in both instances there was excellent selectivity for the propylene oxide and an excellane conversion of the t-amyl hydroperoxide.

In an attempt to broaden the scope of the instant invention, various experiments were run using a hydroperoxide other than TBHP or TAHP—in this case cumene hydroperoxide (CHP). It was surprisingly discovered that while TBHP and CHP behave similarly at high propylene to hydroperoxide mole ratios, at the low ratios of this invention, below about 2:1, their behaviors diverged. The propylene oxide yields using CHP remained low when the propylene to cumene hydroperoxide mole ratios were low in contrast to the propylene oxide yields obtained using TBHP when high catalyst concentrations were used in both instances. When CHP was used in the low ratio examples propylene oxide selectivities, basis CHP reacted, did increase when catalyst concentration increased, but not nearly to the extent that they did when TBHP was used in similar examples. Thus, it was also discovered that the choice of the hydroperoxide is also crucial in obtaining good results, particularly with respect to the method of this invention. This discovery will be explored in detail with respect to the following examples. These examples were conducted according to the procedures outlined earlier using the parameters noted in the tables.

Tables 10 and 11 show the overriding influence of mole ratio of propylene to CHP. When CHP is used, the selectivity to propylene oxide, basis CHP reacted, decreases rapidly with decreasing charge ratios of propylene to CHP. Examples 32-36 demonstrate that with decreasing propylene/CHP charge ratio, propylene oxide selectivity decreases while dimer content (on a "pure PO" basis, i.e. propylene distilled out) generally increases, at low catalyst levels (69-78 ppm). Examples 37 and 38 demonstrate a similar trend for medium catalyst levels (about 250 ppm), while Examples 39-45 reveal that these undesirable results hold true even for catalyst concentrations that are high (400-449 ppm).

With CHP, the propylene dimer make does not decrease with lower propylene/CHP charge ratio as it does with lower propylene/TBHP charge ratios. Actually, the dimer make tends to increase with decreasing initial propylene/CHP ratios. Further, note that Table 10 shows these trends for two different CHP concentrations of CHP in cumyl alcohol, 30 and 59%, and that the lower CHP amount (30%) actually gives better results to PO selectivity.

Table 12 recasts some previous examples in a form which demonstrates that while keeping the propylene/CHP mole charge ratio constant (about 3:1 for Examples 34, 37 and 39, and about 1.3:1 for Examples 35 and 41) and increasing the catalyst levels from the 60-80 ppm molybdenum catalyst range to the 250 to 450 ppm catalyst range, the propylene oxide selectivity, basis CHP reacted, CHP conversion and propylene oxide yields all increase. Even the propylene dimer make decreases. However, also note that for Examples 35 and 41 at low propylene/CHP ratios, propylene oxide selectivities, basis CHP reacted, are still low. Thus, it appears that when CHP is used, high reactant ratios should be maintained, in contrast to the case where TBHP is used and excellent propylene oxide selectivities, basis TBHP reacted, are achievable with low propylene/TBHP mole ratios.

Table 13 presents four previous examples plus two new ones (50 and 51) to demonstrate that, at a given catalyst level (250 or 400-450 ppm), that propylene oxide selectivity, basis CHP reacted, decreases and propylene dimer make increases when the CHP concentration increases from 30 to 59%. Propylene oxide yields also decrease.

Table 14 presents the previous examples recast into yet another form to demonstrate that at propylene/CHP charge ratios of 1.3:1 to 1.4:1 it is impossible to achieve high PO selectivities or yields by varying either the CHP concentration (30.0 to 43 to 59%) or the catalyst concentration (60 to 250 to 450 ppm basis total charge.) In fact, at reactant mole ratios of 1.3:1 to 1.4:1, it appears that the optimum catalyst level may be the 200 to 350 ppm range. Notice that the propylene dimer make increases with decreasing PO selectivity and decreases with increasing PO selectivity. This latter relationship is not seen with TBHP.

The CHP results seen herein are to some extent confirmed by Kollar in U.S. Pat. No. 3,351,635 (see Table 10) where it is seen that CHP conversion and epoxide selectivity decrease with decreasing mole ratio. The invention herein of using high catalyst concentrations was not discovered therein, even to the limited extent possible with CHP, as opposed to the dramatic improvement possible with TBHP.

Finally, an Example 55 was conducted substantially the same as Example 39 except that it was performed in a single one-hour, 90° C. step as opposed to the staged reaction of Example 39 (one hour at 90° C. followed by one hour at 110° C.). Other minor differences were a charge ratio of 7.18:1 instead of 7.03:1 and a catalyst concentration of 79 ppm instead of 78. As with TBHP, the CHP conversion was much lower (66% as compared with Example 39's 97.7%).

TABLE 10

EFFECT OF MOLE RATIO OF PROPYLENE TO CHP ON PROPYLENE OXIDE SELECTIVITY[1]

| Example | Mole Ratio Propylene to CHP | CHP Amount | CHP Amount of Cumene and Others | Catalyst ppm, Basis Total Charge | GLC Analysis PO Conc., Wt. % GLC | GLC Analysis Propylene Dimer on Pure PO Basis | PO Selec. Basis CHP Reacted, % | CHP Conversion, % | Molybdenum Recovery, % | PO Yield, % |
|---|---|---|---|---|---|---|---|---|---|---|
| 32 | 7.03:1 | 43.7 | 6.3 | 78 | 8.78 | 58.6 | 99.9 | 97.7 | 60.8 | 97.6 |
| 33 | 5.00:1 | 43.7 | 6.3 | 77 | 9.00 | 48.7 | 99.1 | 88.0 | 75.7 | 87.2 |
| 34 | 3.03:1 | 43.7 | 6.3 | 78 | 5.99 | 43.0 | 68.3 | 72.1 | 70.5 | 49.2 |
| 35 | 1.32:1 | 42.8 | 7.2 | 69 | 0.99 | 125.7 | 9.5 | 74.3 | 75.6 | 7.0 |
| 36 | 1.19:1 | 43.8 | 5.7 | 72 | 1.07 | 108.0 | 10.4 | 70.7 | 67.0 | 7.3 |
| 37 | 3.12:1 | 43.8 | 5.7 | 248 | 9.09 | 37.3 | 81.2 | 92.9 | 93.8 | 75.4 |
| 38 | 1.35:1 | 43.4 | 6.0 | 250 | 3.28 | 48.9 | 27.3 | 84.9 | 75.4 | 23.2 |
| 39 | 3.07:1 | 43.8 | 5.7 | 400 | 11.03 | 31.2 | 93.5 | 98.0 | 91.5 | 91.6 |
| 40 | 2.16:1 | 43.8 | 5.7 | 447 | 5.75 | 67.2 | 46.4 | 94.8 | 73.4 | 44.0 |
| 41 | 1.34:1 | 43.8 | 5.7 | 449 | 3.23 | 52.9 | 24.7 | 92.1 | 67.4 | 22.8 |

[1]Two-stage reaction throughout, 1 hour at 90° C. followed by 1 hour at 110° c. Catalyst throughout was AHM-2-ethyl-hexanol complex having 3.56% molybdenum. Also, 50% of CHP solution was TBA or other added alcohol. Water content of CHP was 0.6% or less.

TABLE 11

EFFECT OF MOLE RATIO OF PROPYLENE TO CHP ON PROPYLENE OXIDE SELECTIVITY[1]

| Example | Mole Ratio Propylene to CHP | CHP Amount | CHP Amount of Cumene and Others | Catalyst ppm, Basis Total Charge | GLC Analysis PO Conc., Wt. % GLC | GLC Analysis Propylene Dimer on Pure PO Basis | PO Selec. Basis CHP Reacted, % | CHP Conversion, % | Molybdenum Recovery, % | PO Yield, % |
|---|---|---|---|---|---|---|---|---|---|---|
| 42[2] | 2.23:1 | 30.0 | 4.3 | 448 | 5.61 | 61.8 | 61.3 | 96.0 | 96.6 | 58.8 |
| 43[2] | 1.32:1 | 30.0 | 4.3 | 448 | 1.77 | 87.4 | 19.2 | 91.0 | 77.5 | 17.4 |
| 44[3] | 2.08:1 | 59.0 | 8.4 | 448 | 5.36 | 71.9 | 34.3 | 94.0 | 75.2 | 32.2 |
| 45[4] | 1.33:1 | 59.0 | 9.8 | 447 | 2.04 | 222.2 | 11.7 | 95.1 | 67.7 | 11.2 |

[1]Two-stage reaction throughout, 1 hour at 90° C. followed by 1 hour at 110° C. Catalyst throughout was AHM-2-ethyl-hexanol complex having 3.56% molybdenum. Also, water content of CHP was 0.5% or less.
[2]65.1% of CHP solution was TBA or other alcohol.
[3]32.0% of CHP solution was TBA or other alcohol.
[4]31.1% of CHP solution was TBA or other alcohol.

TABLE 12

EFFECT OF INCREASED CATALYST LEVELS ON PROPYLENE OXIDE SELECTIVITY WITH CONSTANT MOLE RATIO[1]

| Example | Mole Ratio Propylene to CHP | Catalyst ppm, Basis Total Charge | GLC Analysis PO Conc. Wt. % GLC | GLC Analysis Propylene Dimer on a Pure PO Basis | PO Selec. Basis CHP Reacted, % | CHP Conversion, % | Molybdenum Recovery, % | PO Yield, % |
|---|---|---|---|---|---|---|---|---|
| 34 | 3.03:1 | 78 | 5.99 | 43.0 | 68.3 | 72.1 | 70.5 | 49.2 |
| 37 | 3.12:1 | 248 | 9.09 | 37.3 | 81.2 | 92.9 | 93.8 | 75.4 |
| 39 | 3.07:1 | 400 | 11.03 | 31.2 | 93.5 | 98.0 | 91.5 | 91.6 |
| 35 | 1.32:1 | 69 | 0.99 | 125.7 | 9.5 | 74.3 | 76.6 | 7.0 |
| 41 | 1.34:1 | 449 | 3.23 | 52.9 | 24.7 | 92.1 | 67.4 | 22.8 |

[1]Two-stage reaction throughout, 1 hour at 90° C. followed by 1 hour at 110° C. Catalyst throughout was AHM 2-ethyl-hexanol complex having 3.56% molybdenum. CHP had from 42.8–43.8% CHP, 50.0% TBA or other added alcohol, 0.0–0.5% water with difference of 5.7–7.2% as cumene and other compounds.

TABLE 13

EFFECT OF CHP CONCENTRATION[1]

| Example | Mole Ratio Propylene to CHP | CHP[2] CHP Content, % | CHP[2] TBA or Other Alcohol Content, % | Catalyst ppm, Basis Total Charge | GLC Analysis PO Conc., Wt. % GLC | GLC Analysis Propylene Dimer on a Pure PO Basis | PO Selec. Basis CHP Reacted, % | CHP Conversion, % | Molybdenum Recovery, % | PO Yield, % |
|---|---|---|---|---|---|---|---|---|---|---|
| 46 | 2.23:1 | 30.0 | 65.1 | 448 | 5.61 | 61.8 | 61.3 | 96.0 | 96.6 | 58.8 |
| 47 | 2.08:1 | 59.0 | 32.0 | 448 | 5.36 | 71.9 | 34.3 | 94.0 | 75.2 | 32.2 |
| 48 | 1.32:1 | 30.0 | 65.1 | 448 | 1.77 | 87.4 | 19.2 | 91.0 | 77.5 | 17.4 |
| 49 | 1.33:1 | 59.0 | 31.1 | 447 | 2.04 | 222.2 | 11.7 | 95.1 | 67.7 | 11.2 |
| 50 | 1.39:1 | 30.0 | 65.1 | 248 | 1.82 | 60.6 | 21.4 | 83.5 | 77.2 | 17.9 |
| 51 | 1.30:1 | 59.0 | 31.4 | 250 | 264 | 125.2 | 16.3 | 87.7 | 86.2 | 14.3 |

[1]Two-stage reaction throughout, 1 hour at 90° C. followed by 1 hour at °110 C. Catalyst throughout was AHM 2-ethyl-hexanol complex having 3.56% molybdenum.
[2]CHP had from 4.3–9.8% cumene and other compounds and 0.6% or less water.

TABLE 14
EXAMPLES SHOWING POOR RESULTS WITH LOW MOLE RATIOS OF PROPYLENE/CHP

| Example | Mole Ratio Propylene to CHP | CHP[2] CHP Content, % | TBA or Other Alcohol Content, % | Catalyst ppm, Basis Total Charge | GLC Analysis PO Conc., Wt. % GLC | Propylene Dimer on a Pure PO Basis | PO Selec. Basis CHP Reacted, % | CHP Conversion, % | Molybdenum Recovery, % | PO Yield, % |
|---|---|---|---|---|---|---|---|---|---|---|
| 50 | 1.39:1 | 30.0 | 65.1 | 248 | 1.82 | 60.6 | 21.4 | 83.5 | 77.2 | 17.9 |
| 48 | 1.32:1 | 30.0 | 65.1 | 448 | 1.77 | 87.4 | 19.2 | 91.0 | 77.5 | 17.4 |
| 35 | 1.32:1 | 42.8 | 50.0 | 69 | 0.99 | 125.7 | 9.5 | 74.3 | 75.6 | 7.0 |
| 38 | 1.35:1 | 43.4 | 50.0 | 250 | 3.28 | 48.9 | 27.3 | 84.9 | 75.4 | 23.2 |
| 41 | 1.34:1 | 43.8 | 50.0 | 449 | 3.23 | 52.9 | 24.7 | 92.1 | 67.4 | 22.8 |
| 51 | 1.30:1 | 59.0 | 31.4 | 250 | 2.64 | 125.2 | 16.3 | 87.7 | 86.2 | 14.3 |
| 49 | 1.33:1 | 59.0 | 31.4 | 447 | 2.04 | 222.2 | 11.7 | 95.1 | 67.7 | 11.2 |

Olefin Choice

Although propylene has been used in the prior examples of the present invention as a matter of convenience and to provide for comparative data, other $C_3$–$C_{20}$ olefins may also be used in the practice of the present invention. This is illustrated by the following specific examples. When the higher olefins such as $C_4$ to $C_{20}$ are epoxidized, it is important to obtain an essentially quantitive conversion of the olefin to the epoxide because the feed stock and epoxide reaction product have similar physical properties and are separated only with great difficulty.

Example 33

To a 1-liter round bottomed Morton (fluted flask equipped with a mechanical stirrer, Dean Stark trap, thermometer, $N_2$ inlet and bubbler, was added 35.31 g of ammonium heptamolybdate tetrahydrate from Climax Molybdenum Co. (molecular weight = 1235.86, g atoms moly = 0.2000, $(NH_4)_6Mo_7O_{24} \cdot 4H_2O$) followed by 182.32 g of 2-ethyl-1-hexanol (99% purity, alfa, molecular weight = 130.2, moles = 1.4) and 14.4 ml $H_2O$. Note the mole ratio of alcohol (2-ethyl-1hexanol) to g atoms molybdenum = 7.0/1 and the mole ratio of added $H_2O$/g atoms molybdenum = 4.0/1. The reaction mixture was heated slowly to 178° C. and held at 178–180° C. for five hours during which time 29 ml H2O were removed with the Dean Stark trap. The cooled reaction mixture was filtered through glass filter paper to remove solids. The filtrate weight 176.3 g.

| | | |
|---|---|---|
| % molybdenum in filtrate by AA | = | 10.1% |
| % N in filtrate by Kjeldahl | = | 0.34% |
| g molybdenum fed | = | 19.187 |
| g moly "out" in (soluble) filtrate | = | 17.81 |
| % molybdenum incorporated in catalyst | = | 92.80% |

Example 34

To a 250 ml round-bottomed flask fitted with magnetic stirring bar, thermometer, condenser, $N_2$ inlet and bubbler was added 42.0 g of octene-1 (molecular weight 112, 0.375 moles) followed by 35.5 g of 72.08% TBHP with 0.39 g of molybdenum catalyst 5810-60 (10.1% molybdenum) premixed with the TBHP/TBA. The reaction mixture was heated slowly to 95° C. (exothermed to 99° C.) and then held there (93–96° C.) for 2.0 hours. After cooling, the reaction mixture was solids free and weighed 74.1g.

| | | |
|---|---|---|
| wt. % TBHP | = | 1.70% |
| wt. % octene oxide | = | 46.182 |
| wt. % octene | = | 12.677% |
| g octene oxide | = | 34.221 |
| moles epoxide | = | 0.26735 |

$$\text{Selectivity } C_8 \text{ epoxide} = \frac{0.26785}{1.2703} = 98.91\%$$

$$\text{Yield } C_8 \text{ epoxide} = \frac{0.26735}{0.2843} = 94.03\%$$

| | | |
|---|---|---|
| g TBHP remaining | = | 1.2597 |
| moles TBHP remaining | = | 0.0140 |
| moles TBHP fed | = | 0.2843 |
| moles TBHP reacted | = | .2703 |

$$\text{Conversion TBHP} = \frac{.2703}{.2843} = 95.08\%$$

Several other examples are given in the table attached. The procedures and apparatus were exactly like that in Example 34.

TABLE 15
EPOXIDATION OF OCTENE WITH TBHP (72.1% TBHP, 0.2% WATER, 27.7% TBA)

| Run No. | N. B. Run # | Olefin TBHP Mole Ratio | Rxn Temp., °C. | Rxn Time, Hours | Cat. Wt. % Moly Basis Total Charge | GLC-Product Wt. % Octene Unreacted (Dodecene) | Wt. % Oxide Formed (Dodecene oxide) | Wt. % TBHP Remaining Unreacted | Basis TBHP Reacted Selectivity to $C_8$ Epoxide or $C_{12}$ Epoxide | TBHP Conv. | Basis TBHP Fed Yield of $C_8$ Epoxide ($C_{12}$ Epoxide) | Conversion of Octene (Dodecene) | Olefin Used |
|---|---|---|---|---|---|---|---|---|---|---|---|---|---|
| 52 | 5850-33 | 5.9/1 | 95 | 2.0 | .0185 | 68.35 | 15.71 | 0.025 | 92.9 | 99.8 | 92.7 | 21.8 | 0 |
| 53 | 5850-32 | 3.9/1 | 95 | 2.0 | .0185 | 56.13 | 22.53 | 0.04 | 93.8 | 99.8 | 93.6 | 31.7 | 0 |
| 54 | 5850-31 | 1.95/1 | 95 | 2.0 | .0185 | 29.86 | 37.31 | 0.75 | 99.5 | 97.2 | 96.8 | 54.6 | 0 |
| 55 | 5850-8 | 1.32/1 | 95 | 2.0 | .0506 | 12.68 | 46.18 | 1.70 | 98.9 | 95.1 | 94.0 | 77.6 | 0 |
| 56 | 5850-45 | 1.08/1 | 110 | 2.0 | .0185 | 5.71 | 48.00 | 2.55 | 99.3 | 93.0 | 92.4 | 88.4 | 0 |
| 57 | 5850-5 | 1.08/1 | 95 | 4.0 | .0493 | 4.89 | 50.07 | 2.47 | 95.9 | 93.7 | 89.9 | 90.7 | 0 |

TABLE 15-continued
EPOXIDATION OF OCTENE WITH TBHP (72.1% TBHP, 0.2% WATER, 27.7% TBA)

| Run No. | N. B. Run # | Olefin TBHP Mole Ratio | Rxn Temp., °C. | Rxn Time, Hours | Cat. Wt. % Moly Basis Total Charge | GLC-Product Wt. % Octene Unreacted (Dodecene) | GLC-Product Wt. % Oxide Formed (Dodecene oxide) | Wt. % TBHP Remaining Unreacted | Basis TBHP Reacted Selectivity to $C_8$ Epoxide or $C_{12}$ Epoxide | TBHP Conv. | Basis TBHP Fed Yield of $C_8$ Epoxide ($C_{12}$ Epoxide) | Conversion of Octene (Dodecene) | Olefin Used |
|---|---|---|---|---|---|---|---|---|---|---|---|---|---|
| 58 | 5858-51 | 1.08/1 | 110 / 135 | 1.0 / 1.0 | .0185 | 4.64 | 45.49 | 1.73 | 92.0 | 95.3 | 87.6 | 90.6 | 0 |
| 59 | 5850-50 | 1.00/1 | 110 / 135 | 1.0 / 1.0 | .0185 | 2.80 | 47.52 | 2.05 | 93.3 | 94.6 | 88.3 | 94.1 | 0 |

TABLE 16
EPOXIDATION OF DODECENE WITH TBHP (72.1% TBHP, 0.2% WATER, 27.7% TBA)

| Run No. | N. B. Run # | Olefin TBHP Mole Ratio | Rxn Temp., °C. | Rxn Time, Hours | Cat. Wt. % Moly Basis Total Charge | GLC-Product Wt. % Octene Unreacted (Dodecene) | GLC-Product Wt. % Oxide Formed (Dodecene oxide) | Wt. % TBHP Remaining Unreacted | Basis TBHP Reacted Selectivity to $C_8$ Epoxide or $C_{12}$ Epoxide | TBHP Conv. | Basis TBHP Fed Yield of $C_8$ Epoxide ($C_{12}$ Epoxide) | Conversion of Octene (Dodecene) | Olefin Used |
|---|---|---|---|---|---|---|---|---|---|---|---|---|---|
| 60 | 5850-48 | 0.96/1 | 110 | 2.0 | .0185 | 3.78 | 45.90 | 4.77 | 95.3 | 87.6 | 83.6 | 90.6 | 0 |
| 61 | 5850-57 | 1.08/1 | 95–105 | 2.0 | .0185 | (10.28) | (51.65) | 4.10 | (96.7) | 86.4 | (83.6) | (83.2) | D.D. |
| 62 | 5850-54 | 1.08/1 | 110 / 135 | 1.0 / 1.0 | .0185 | (6.48) | (56.25) | 0.87 | (97.0) | 97.0 | (94.1) | (89.1) | D.D. |
| 63 | 5850-55 | 1.00/1 | 95–110 | 2.0 | .0185 | (7.27) | (54.34) | 4.01 | (95.1) | 87.5 | (84.1) | (87.8) | D.D. |
| 64 | 5850-53 | 1.00/1 | 110 / 135 | 1.0 / 1.0 | .0185 | (3.17) | (56.05) | 1.75 | (94.8) | 94.3 | (89.4) | (94.5) | D.D. |
| 65 | 5850-52 | 0.96/1 | 110 / 135 | 1.0 / 1.0 | .0185 | (3.24) | (55.25) | 1.97 | (93.4) | 93.6 | (87.4) | (94.2) | D.D. |

Many modifications could be made by one skilled in the art in the invention without changing its spirit or scope which are defined only by the appended claims.

What is claimed is:

1. In a method wherein a hydroperoxide charge stock selected from the group consisting of t-butyl hydroperoxide and t-amyl hydroperoxide is reacted in a reaction zone in liquid phase with a $C_3$ to $C_{20}$ olefin charge stock in the presence of a catalytically effective amount of a soluble molybdenum catalyst to form a product olefin epoxide corresponding to the olefin charge stock and a product alcohol selected rom the group consisting of t-butyl alcohol and t-amyl alcohol corresponding to the hydroperoxide charge stock, the improvement which comprises:

maintaining in said reaction zone a reaction medium containing less than about 1 wt. % of water and comprising said olefin charge stock, and more than 60 wt. % of polar components comprising said corresponding product olefin epoxide, said hydroperoxide charge stock, said corresponding product alcohol, said water and said catalyst, by feeding to said reaction zone at least a 30 wt. % solution of said hydroperoxide charge stock in solution in aid corresponding product alcohol, and feeding said olefin charge stock to said reaction zone in an amount relative to the hydroperoxide charge stock in said solution such that the mole ratio of said olefin charge stock to said hydroperoxide charge stock is within the range of about 0.5 to about 2 moles of olefin charge stock per mole of hydroperoxide charge stock, and maintaining reaction conditions in said reaction zone including a reaction temperature of about 50° to about 150° C., a reaction time of about 0.5 to about 4 hours and a catalyst concentration in solution in said reaction medium of about 50 to about 1,000 ppm of molybdenum.

2. A method in claim 1 wherein the peroxide is t-butyl hydroperoxide and the corresponding product alcohol is t-butyl alcohol.

3. A method as in claim 2 wherein the olefin charge is octene and the corresponding olefin epoxide is octene epoxide.

4. A method as in claim 2 wherein the olefin charge is dodecene and the corresponding olefin epoxide is dodecene epoxide.

5. A method as in claim 1 wherein the peroxide charge is composed of t-amyl peroxide and the corresponding product alcohol is t-amyl alcohol.

6. In a method wherein a hydroperoxide charge stock selected from the group consisting of t-butyl hydroperoxide and t-amyl hydroperoxide is reacted in a reaction zone in liquid phase with a propylene charge stock in the presence of a catalytically effective amount of a soluble molybdenum catalyst to form propylene oxide and a product alcohol selected from the group consisting of t-butyl alcohol and t-amyl alcohol corresponding to the hydroperoxide charge stock, the improvement which comprises:

maintaining in said reaction zone a reaction medium containing less than about 1 wt. % of water and comprising said propylene charge stock, and more than 60 wt. % of polar components comprising said propylene oxide, said hydroperoxide charge stock, said corresponding product alcohol, said water and said catalyst, by feeding to said reaction zone at least a 30 wt. % solution of said hydroperoxide charge stock in solution in said corresponding product alcohol, and feeding said propylene charge stock to said reaction zone in an amount relative to the hydroperoxide charge stock in said solution such that the mole ratio of said propylene charge stock to the said hydroperoxide charge stock is within the range of about 0.5 to about 2 moles of propylene per mole of peroxide charge stock, and maintaining reaction conditions in said reaction zone including a reaction temperature of about 50° to about 150° C., a reaction time of about 0.5 to about 4 hours and a catalyst concentration in solution in said reaction medium of about 50 to about 1,000 ppm of molybdenum.

7. A method as in claim 6 wherein the peroxide charge is composed of t-amyl peroxide and the corresponding product alcohol is t-amyl alcohol.

8. In a method wherein a t-butyl hydroperoxide charge stock is reacted in a reaction zone in liquid phase with a propylene charge stock in the presence of a catalytically effective amount of a soluble molybdenum catalyst to form propylene oxide and t-butyl alcohol, the improvement which comprises:

maintaining in said reaction zone a reaction medium containing less than about 1 wt. % of water and comprising said propylene charge stock, and more than 60 wt. % of polar components comprising said propylene oxide, said t-butyl hydroperoxide charge stock, said t-butyl alcohol, said water and said catalyst, by feeding to said reaction zone at least a 30 wt. % solution of said t-butyl hydroperoxide charge stock in solution in said t-butyl alcohol, and feeding said propylene charge stock to said reaction zone in an amount relative to the amount of t-butyl hydroperoxide charge stock in said solution such that the mole ratio of said propylene charge stock to said t-butyl hydroperoxide charge stock in said charged solution is within the range of bout 0.5 to about 2 moles of propylene per mole of t-butyl hydroperoxide, maintaining reaction conditions in said reaction zone including a reaction temperature of about 90° to about 140° C., a reaction of about 0.5 to about ∝ hours and a catalyst concentration in solution in said reaction medium of about 200 to about 600 ppm of molybdenum.

9. A method as in claim 8 wherein the solubilized molybdenum catalyst concentration in said reaction medium is within the range of about 250 to about 500 ppm and the reaction temperature is within the range of about 100° to about 130° C.

10. A method as in claim 8 wherein the catalyst concentration is within the range of about 250 to about 500 ppm, the reaction temperature is within the range of about 100° to about 130° C. and the reaction time is within the range of about 1.5 to about 2.0 hours.

11. A method as in claim 8 wherein the catalyst concentration is within the range of about 250 to 500 ppm, the reaction temperature is within the range of about 110° to about 120° C. and the reaction time is about 2.0 hours.

12. In a continuous method wherein t-butyl hydroperoxide is continuously reacted in a reaction zone in liquid phase with agitation with propylene in the presence of a catalytically effective amount of a soluble molybdenum catalyst to form propylene oxide and t-butyl alcohol the improvement which comprises:

conducting said reaction in said reaction zone for an average residence time of about 0.5 to 4 hours at a temperature within the range of about 100° to about 130° C. in a reaction medium containing less than about 1 wt. % of water and about 200 to about 600 ppm of catalyst and composed of said propylene, said propylene oxide, said t-butyl peroxide, said t-butyl alcohol, said water, and said catalyst, maintaining a reaction medium in said reaction zone composed of more than 60 wt. % of polar components by continuously charging to said reaction zone a solution of said t-butyl hydroperoxide in said t-butyl alcohol containing at least about 30 wt. % of said t-butyl hydroperoxide, continuously charging said propylene in an amount relative to the charge of t-butyl hydroperoxide in said solution such that the mole ratio of said propylene to said t-butyl hydroperoxide in said solution is within the range of about 0.5 to about 2 moles of propylene per mole of t-butyl hydroperoxide, and continuously removing a product stream from said reaction zone and recovering propylene oxide and t-butyl alcohol from said product stream, said polar components of said reaction medium comprising said t-butyl hydroperoxide, said t-butyl alcohol, said water, said catalyst and said propylene oxide.

13. A continuous method as in claim 12 wherein said t-butyl hydroperoxide and said propylene are initially reacted with each other in a first continuous stirred tank reaction zone to give an intermediate reaction mixture, and wherein a stream of said intermediate reaction mixture is continuously withdrawn from said continuously stirred tank reaction zone and charged to a plug flow reaction zone and wherein the said reaction is completed in said plug flow reaction zone.

14. A method as in claim 13 wherein the continuously stirred tank reactor is operated at a temperature within the range of about 70° to about 115° C. and the second reactor is operated at a temperature within the range of about 115° to about 150° C.

15. A method as in claim 14 wherein the continuously stirred tank reactor is operated at a temperature of 90° to 115° C. and the second reactor is operated at a temperature within the range of about 120° to 140° C.

16. A method as in claim 15 wherein the mole ratio of the propylene to the t-butyl hydroperoxide is within the range of about 0.9 to about 1.8 moles of propylene per mole of t-butyl hydroperoxide.

17. A method as in claim 16 wherein the mole ratio is within the range of about 1.05 to about 1.35 moles of propylene per mole of t-butyl hydroperoxide.

18. In a method wherein t-butyl hydroperoxide is reacted in a reaction zone in liquid phase with propylene in the presence of a catalytically effective amount of a soluble molybdenum catalyst to form propylene oxide and t-butyl alcohol, the improvement which comprises:

maintaining a reaction medium composed of more than 60 wt. % of polar components in a reaction medium in said reaction zone consisting essentially of said propylene, said propylene oxide, said t-butyl hydroperoxide, said t-butyl alcohol, less than about 1 wt. % of water, and said catalyst, by feeding to said reaction zone a solution of said t-butyl hydroperoxide in said t-butyl alcohol containing about 40 to about 75 wt. % of said t-butyl hydroperoxide, and feeding said propylene to said reaction zone in an amount relative to the amount of t-butyl hydroperoxide in said solution such that the mole ratio of said propylene to said t-butyl hydroperoxide in said solution is within the range of about 0.5 to about 2 moles of propylene per mole of t-butyl hydroperoxide, and maintaining reaction conditions in said reaction zone including a reaction temperature of about 90° to about 140° C., a reaction time of about 0.5 to about 4 hours and a catalyst concentration in solution in said reaction medium of about 200 to about 600 ppm of molybdenum, said polar components of said reaction medium consisting essentially of said t-butyl hydroperoxide, said t-tertiary butyl alcohol, said water, said catalyst and said propylene oxide.

19. In a continuous method wherein t-butyl hydroperoxide is continuously reacted in a liquid reaction medium with propylene in the presence of a catalytically effective amount of a solubilized molybdenum catalyst to form propylene oxide and t-butyl alcohol, said reaction medium containing less than about 1 wt. % of water and consisting essentially of said propylene, said propylene oxide, said t-butyl hydroperoxide, said t-butyl alcohol, said catalyst, and said water, and wherein said reaction between said t-butyl hydroperoxide and said propylene is initiated in a first continuous stirred tank reaction zone to provide an intermediate reaction mixture, and wherein a stream of said intermediate reaction mixture is continuously withdrawn from said continuously stirred tank reaction zone and charged to a plug flow reaction zone and wherein said reaction between said t-butyl hydroperoxide and said propylene is completed in said plug flow reaction zone, the improvement for obtaining about a 96% to 99% conversion of said t-butyl hydroperoxide with about a 96% to 99% selectivity to propylene oxide on the basis of t-butyl hydroperoxide reacted which comprises:

initiating said reaction in said continuous stirred tank reaction zone in the presence of about 200 to about 600 ppm of said solubilized molybdenum catalyst under reaction conditions including a temperature of about 90° to about 115° C. for an average residence time in said continuous stirred tank reaction zone within the range of about 0.5 to about 1.5 hours such that about 30 wt. % to about 50 wt. % of said t-butyl hydroperoxide is converted in said continuous stirred tank reaction zone, to thereby provide said intermediate reaction mixture, completing said conversion of said t-butyl hydroperoxide in said plug flow reaction zone in the presence of about 200 to about 600 ppm of said solubilized molybdenum catalyst at a temperature within the range of about 115° to about 140° C. and an average residence time of about 0.5 to about 1.5 hours, maintaining a liquid reaction medium in said continuous stirred tank reaction zone and said plug flow reaction zone composed of more than 60 wt. % of polar components by continuously charging to said continuous stirred tank reaction zone a solution of said t-butyl hydroperoxide in said t-butyl alcohol containing about 40 wt. % to about 75 wt. % of said t-butyl hydroperoxide, continuously charging said propylene to said continuous stirred tank reaction zone in an amount relative to the charge of said t-butyl hydroperoxide in said solution such that the mole ratio of said propylene to said t-butyl hydroperoxide is within the range of about 0.5 to about 2 moles of propylene per mole of t-butyl hydroperoxide, and continuously removing a product stream form said plug flow reaction zone and recovering propylene oxide and t-butyl alcohol from said product stream.

20. A method as in claim 19 wherein the continuously stirred tank reaction zone is operated at a temperature within the range of about 100° to about 110° C. and the second plug flow reaction zone is operated at a temperature within the range of about 120° to about 140° C.

21. A method as in claim 19 wherein the propylene and the solution of t-butyl hydroperoxide in t-butyl alcohol are continuously charged to said continuous stirred tank reaction zone in amounts such that the mole ratio of propylene charged to t-butyl hydroperoxide charged is maintained within the range of about 0.9 to about 1.8 moles of propylene charged per mole of t-butyl hydroperoxide charged.

22. A method as in claim 21 wherein the propylene and the solution of t-butyl hydroperoxide in t-butyl alcohol are continuously charged to said continuous stirred tank reaction zone in amounts such that the mole ratio of propylene charged to t-butyl hydroperoxide charged is maintained within the range of about 1.05 to about 1.35 moles of propylene charged per mole of t-butyl hydroperoxide charged.

23. In a continuous method wherein t-butyl hydroperoxide is continuously reacted in a reaction zone in liquid phase with propylene in the presence of a catalytically effective amount of a soluble molybdenum catalyst to form propylene oxide and t-butyl alcohol the improvement which comprises:

conducting said reaction in said reaction zone for an average residence time of about 0.5 to 4 hours at a temperature within the range of about 100° to about 130° C. in a reaction medium free from added basic substances and added free radical inhibitors and consisting essentially of less than about 1 wt. % of water, about 200 to about 600 ppm of catalyst, said propylene, said propylene oxide, said t-butyl peroxide, and said t-butyl alcohol, said reaction medium being composed of from about 65 to about 75 wt. % of polar components, maintaining the polarity of said reaction medium by continuously charging to said reaction zone a solution of said t-butyl hydroperoxide in said t-butyl alcohol containing from about 40 to about 75 wt. % of said t-butyl hydroperoxide, and by continuously charging said propylene in an amount relative to the charge of t-butyl hydroperoxide in said solution such that the mole ratio of said propylene to said t-butyl hydroperoxide in said solution is within the range of about 0.5 to about 2 moles of propylene per mole of t-butyl hydroperoxide, and continuously removing a product stream from said reaction zone and recovering propylene oxide and t-butyl alcohol from said product stream, said polar components of said reaction medium comprising said t-butyl hydroperoxide, said t-butyl alcohol, said water, said catalyst and said propylene oxide.

24. A method as in claim 23 wherein said propylene is continuously charged to said reaction zone in an amount relative to the charge of t-butyl hydroperoxide in said solution to said reaction zone such that the mole ratio of said charged propylene to said charge of t-butyl hydroperoxide in said solution is within the range of about 0.9:1 to about 1.8:1 moles of propylene per mole of t-butyl hydroperoxide.

25. A method as in claim 23 wherein said propylene is continuously charged to said reaction zone in an amount relative to the charge of t-butyl hydroperoxide in said solution to said reaction zone such that the mole ratio of said charged propylene to said charge to t-butyl hydroperoxide in said solution is within the range of about 1.05:1 to about 1.35:1 moles of propylene per mole of t-butyl hydroperoxide.

* * * * *

UNITED STATES PATENT AND TRADEMARK OFFICE
CERTIFICATE OF CORRECTION

PATENT NO.    :   4,891,437

DATED         :   January 2, 1990

INVENTOR(S)   :   Edward T. Marquis, Kenneth P. Keating, John F. Knifton,
                  John R. Sanderson, and Jonathan P. Lustri It is certified that error appears in the above-identified patent and that said Letters Patent is hereby corrected as shown below:

On the face of the patent, in

Related U.S. Application Data [63],
   delete "687,790" and substitute
   therefore --687,690--.

Signed and Sealed this

Twenty-ninth Day of January, 1991

Attest:

HARRY F. MANBECK, JR.

*Attesting Officer*    *Commissioner of Patents and Trademarks*